US 6,427,686 B2

(12) United States Patent
Augustine et al.

(10) Patent No.: US 6,427,686 B2
(45) Date of Patent: Aug. 6, 2002

(54) AIRWAY DEVICE WITH PROVISION FOR COUPLING TO AN INTRODUCER

(75) Inventors: Scott Douglas Augustine, Bloomington; Randall Charles Arnold, Minnetonka; Thomas Wayne McGrail, Chaska, all of MN (US)

(73) Assignee: Augustine Medical, Inc., Eden Prairie, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/199,540

(22) Filed: Nov. 25, 1998

Related U.S. Application Data

(63) Continuation-in-part of application No. 08/730,791, filed on Oct. 16, 1996, now Pat. No. 5,937,859.

(51) Int. Cl.⁷ .............................................. A61M 16/00
(52) U.S. Cl. ............................ 128/200.26; 128/207.14; 128/207.15
(58) Field of Search ................. 128/200.26, 206.29, 128/207.13, 207.14, 207.15, 207.18; 604/264, 280, 282, 283; 606/108, 196; 600/185, 194, 195

(56) References Cited

U.S. PATENT DOCUMENTS

| 614,854 | A | * | 11/1898 | Kratzmueller | 606/196 |
|---|---|---|---|---|---|
| 724,046 | A | * | 3/1903 | Sampson | 606/196 |
| 3,154,069 | A | * | 10/1964 | Ring | 128/200.26 |
| 3,930,507 | A | * | 1/1976 | Berman | 128/200.26 |
| 4,054,135 | A | * | 10/1977 | Berman | 128/200.26 |
| 4,067,331 | A | * | 1/1978 | Berman | 128/200.26 |
| 4,068,658 | A | * | 1/1978 | Berman | 128/200.26 |
| 4,069,820 | A | * | 1/1978 | Berman | 128/200.26 |
| 4,211,234 | A | * | 7/1980 | Fisher | 128/200.26 |
| 4,329,983 | A | * | 5/1982 | Fletcher | 128/207.14 |
| 4,351,342 | A | | 9/1982 | Wiita et al. | |
| 4,509,514 | A | | 4/1985 | Brain | |
| 4,672,960 | A | * | 6/1987 | Frankel | 128/200.26 |
| 4,727,872 | A | * | 3/1988 | Hawk | 128/207.14 |
| 4,825,858 | A | * | 5/1989 | Frankel | 128/200.26 |

(List continued on next page.)

FOREIGN PATENT DOCUMENTS

| DE | P44 47 186.6 | | 12/1994 | | |
|---|---|---|---|---|---|
| EP | 0 389 272 A2 | | 3/1990 | | |
| EP | 0 533 371 A2 | | 9/1992 | | |
| GB | 478958 | | 1/1938 | | |
| WO | WO 95/32754 | | 12/1995 | | |
| WO | WO 97/12640 | | 4/1997 | | |
| WO | WO 97/12641 | | 4/1997 | | |
| WO | WO 98/16273 | | 4/1998 | | |
| WO | WO98/16273 | * | 4/1998 | | 128/200.26 |

OTHER PUBLICATIONS

Partial Search Report for PCT/US99/23269.
International Search Report for PCT/US97/16838.

*Primary Examiner*—John G. Weiss
*Assistant Examiner*—Joseph F. Weiss, Jr.
(74) *Attorney, Agent, or Firm*—Gray Cary; Ware & Freidenrich

(57) ABSTRACT

A laryngeal airway device for sealing against the laryngeal opening includes an air tube with proximal and distal ends and a sealing member attached to the distal end. The sealing member includes a coupler for coupling the device to an introducer. Complementing the laryngeal airway device is an introducer that includes a track for receiving the coupler of the laryngeal airway device and guiding the sealing member to a sealing position with respect to the laryngeal inlet. The introducer may include an epiglottic engager on a distal end to engage the epiglottis and retain it while the sealing member is being tracked to engagement with the laryngeal inlet.

3 Claims, 17 Drawing Sheets

U.S. PATENT DOCUMENTS

| | | | | |
|---|---|---|---|---|
| 4,832,020 A | * | 5/1989 | Augustine | 128/207.14 |
| 4,949,716 A | * | 8/1990 | Chenoweth | 128/207.14 |
| 4,976,261 A | | 12/1990 | Gluck et al. | |
| 4,982,729 A | * | 1/1991 | Wu | 128/200.26 |
| 4,995,388 A | | 2/1991 | Brain | |
| 5,038,766 A | * | 8/1991 | Parker | 128/200.26 |
| 5,042,469 A | * | 8/1991 | Augustine | 128/200.26 |
| 5,092,314 A | * | 3/1992 | Zeitels | 606/196 |
| 5,174,283 A | * | 12/1992 | Parker | 128/200.26 |
| 5,178,132 A | * | 1/1993 | Mahefky | 606/196 |
| 5,203,320 A | * | 4/1993 | Augustine | 128/200.26 |
| 5,241,956 A | | 9/1993 | Brain | |
| 5,259,371 A | | 11/1993 | Tonrey | |
| 5,277,178 A | * | 1/1994 | Dingley | 128/200.26 |
| 5,287,848 A | * | 2/1994 | Cubb et al. | 128/200.26 |
| 5,303,697 A | | 4/1994 | Brain | |
| 5,305,743 A | | 4/1994 | Brain | |
| 5,329,940 A | * | 7/1994 | Adair | 128/200.26 |
| 5,355,879 A | | 10/1994 | Brain | |
| 5,363,838 A | * | 11/1994 | George | 126/11 |
| 5,443,063 A | | 8/1995 | Greenberg | |
| 5,477,851 A | | 12/1995 | Callaghan et al. | |
| 5,494,029 A | | 2/1996 | Lane et al. | |
| 5,498,231 A | * | 3/1996 | Franicevic | 600/190 |
| 5,509,408 A | * | 4/1996 | Kurtis | 128/207.14 |
| 5,513,627 A | | 5/1996 | Flam | |
| 5,529,582 A | | 6/1996 | Fukuhara | |
| 5,584,290 A | | 12/1996 | Brain | |
| 5,623,921 A | | 4/1997 | Kinsinger et al. | |
| 5,632,271 A | | 5/1997 | Brain | |
| 5,638,813 A | * | 6/1997 | Augustine | 128/207.15 |
| 5,655,528 A | | 8/1997 | Pagan | |
| 5,682,880 A | * | 11/1997 | Brain | 128/207.15 |
| 5,850,832 A | * | 12/1998 | Chu | 128/200.26 |
| 5,896,858 A | * | 4/1999 | Brain | 128/207.15 |
| 5,937,859 A | * | 8/1999 | Augustine et al. | 128/207.15 |
| 5,983,897 A | * | 11/1999 | Pagan | 128/207.15 |
| 5,988,167 A | * | 11/1999 | Kamen | 128/207.15 |
| 6,003,510 A | * | 12/1999 | Annunta | 128/200.26 |
| 6,012,452 A | * | 1/2000 | Pagan | 128/200.26 |
| 6,053,166 A | * | 4/2000 | Gomez | 128/200.26 |
| 6,070,581 A | * | 6/2000 | Augustine et al. | 128/207.15 |
| 6,119,695 A | * | 9/2000 | Augustine et al. | 128/207.15 |

* cited by examiner

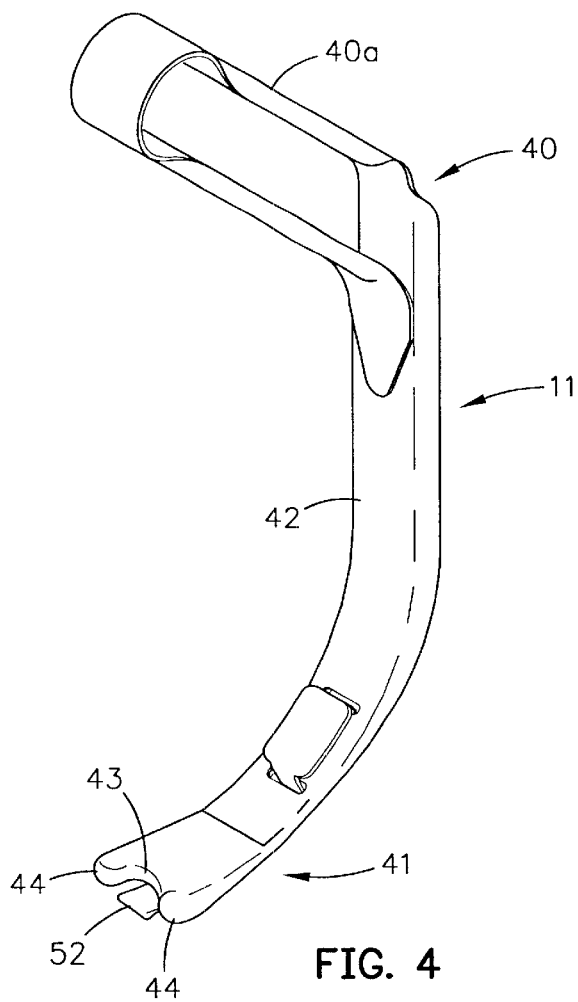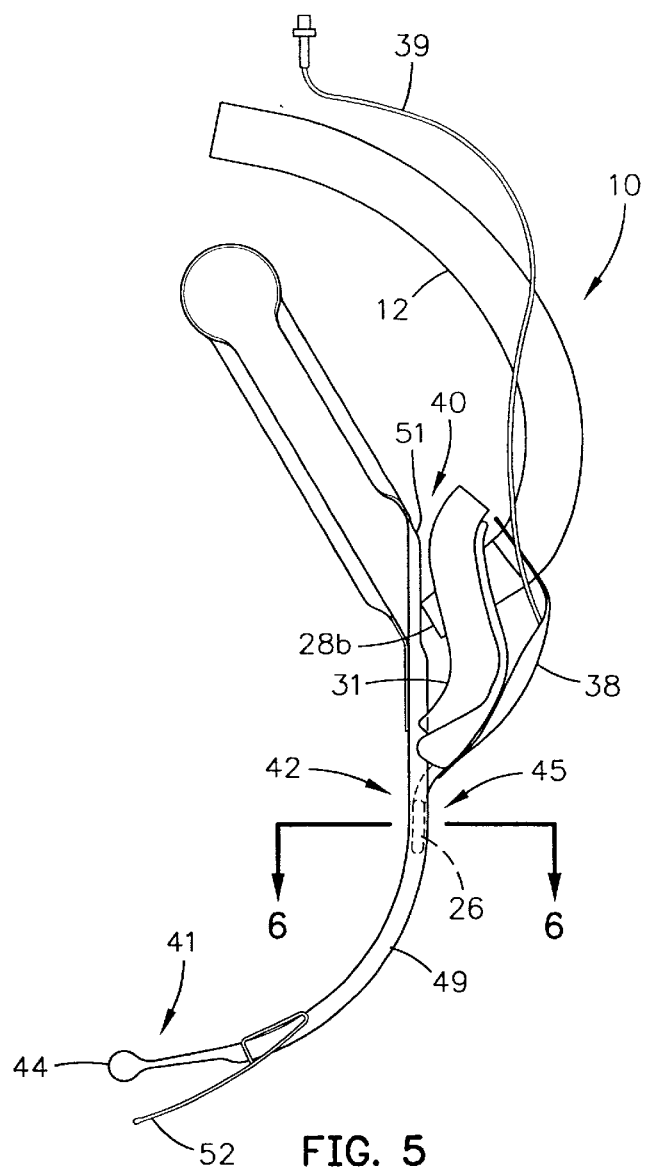

AIRWAY DEVICE WITH PROVISION FOR COUPLING TO AN INTRODUCER

CROSS-REFERENCE TO RELATED APPLICATION

This application is a continuation-in-part of U.S. patent application Ser. No. 08/730,791, filed Oct. 16, 1996 and entitled LARYNGEAL AIRWAY DEVICE, now U.S. Pat. No. 5,937,859.

This application contains subject matter that is related to the following patent applications:

U.S. patent application Ser. No. 08/885,682, filed Jun. 30, 1997, now U.S. Pat. No. 6,070,581, for LARYNGEAL AIRWAY DEVICE;

PCT Application No. US97/16838, filed Sept. 24, 1997, published on Apr. 23, 1998 as WO 98/16273 for LARYNGEAL AIRWAY DEVICE; and U.S. patent application Ser. No. 09/199,909, filed Nov. 25, 1998, now U.S. Pat. No. 6,119,695, for AIRWAY DEVICE WITH PROVISION FOR LATERAL ALIGNMENT, DEPTH POSITIONING, AND RETENTION IN AN AIRWAY.

BACKGROUND OF THE INVENTION

1. Field of the Invention

This invention is concerned with the management of a human airway in order to control respiration. More particularly, the invention concerns a device that brings an airway tube reliably and safely into communication with the laryngeal opening, the upper end of the trachea, which is the breathing passageway that leads to the lungs. The device seats in the throat immediately adjacent the laryngeal opening, tensions and erects the laryngeal opening, and seals with it to provide a channel through the airway tube for artificial ventilation of the lungs. In particular, the invention concerns a laryngeal airway device that can be coupled to an introducer and guided to this position through the throat. For this purpose a tracking introducer is provided.

The invention also concerns a laryngeal blade used to access the laryngeal anatomy in order to support access to the laryngeal opening by an airway device.

Another concern of interest in consideration of the invention is engagement and control of the epiglottis as an aid in gaining access to the laryngeal anatomy.

2. Description of the Related Art

An airway device facilitates ventilation of the lungs of a person. The purpose of such a device is to provide an air pathway from an external air source, through the mouth, throat, and trachea, to the lungs. Additionally, some airway devices provide a seal with the throat of a person, which allows positive pressure ventilation and which may also prevent the leakage of stomach contents into the trachea (aspiration).

It is useful to divide airway devices into two categories: those that pass through the vocal chords and are commonly referred to as "tracheal tubes", and those that lodge in the throat, above the vocal chords, and are commonly referred to as "airways". We shall limit "airway" to refer to a device that provides a fluid pathway from outside the mouth of a person to a location above the vocal chords.

In the variety of airway devices that are available, some merely support the tissue of the pharynx (throat), particularly the tongue, creating a passageway so that air can pass by and into the pharyngeal space toward the laryngeal opening, which is the opening into the voice box. Other airway devices include a tube that provides an air channel to a location near the laryngeal opening. Still other airway devices add a sealing means to the distal end of the tube in order to provide some degree of sealing between the tube and the airway of the person.

A laryngeal mask is an example of a sealing airway device. U.S. Pat. Nos. 4,509,514; 4,995,388; and 5,355,879 are descriptive of a laryngeal mask. A laryngeal mask includes an inflatable doughnut-shaped balloon which, when inflated, circles the laryngeal opening and creates a fluid seal between the outside of the inflated balloon and the tissues in the pharyngeal structures of the throat that surround the larynx.

Another sealing airway device, described in U.S. Pat. No. 5,513,627, includes an inflatable balloon fixed on the distal end of a tracheal tube that is inserted into and inflated within the trachea, forming a seal against the interior walls of the trachea.

In the first three cross-referenced patent applications, all assigned to the assignee of this application and incorporated in their entirety by this reference, a sealing member is mounted near the distal end of an airway tube to seal directly with the rim of the laryngeal opening, portions of the epiglottis, and the sidewalls of the larynx. This unique airway creates a fluid seal directly with the larynx.

Accurate placement of an airway device can be a very difficult task for the clinician and a traumatic event for the patient. When a patient is under anesthesia, or has lost consciousness for other reasons, the tongue and tissues of the throat relax and fall back, effectively obstructing the flow air from the mouth or nose to the laryngeal opening. This same relaxation of the tongue makes it difficult to pass an airway device along the back of the tongue, into the throat. Frequently, the clinician's fingers must be inserted into the patient's mouth to displace the tongue or push the airway device around the corner at the posterior pharynx. Furthermore, the highly variable and extremely flexible anatomy surrounding the larynx make accurate positioning of an airway device very difficult. In particular, the epiglottis must be correctly positioned in order to introduce and seat an airway device that effectively seals against the laryngeal opening. An epiglottis that covers the larynx will prevent a proper seal. Finally, the mucosal tissues lining the mouth, throat, and larynx are very fragile. Devices that are inserted blindly frequently scrape these tissues causing bleeding, sore throats, and throat infections.

Accordingly there is need for easy guidance of an airway device through the mouth and throat that will result in accurate positioning of the device with respect to the larynx.

Accordingly, there is a need for a device that will provide access to the laryngeal anatomy for the purpose of airway management.

Accordingly, there is a need for a laryngeal access device with provision for engagement and control of the epiglottis.

SUMMARY OF THE INVENTION

A sealing laryngeal airway device forms a fluid seal against the rim of the laryngeal opening, that is, against the larynx itself. The invention provides for guiding or tracking such a device through the throat to the laryngeal opening.

The invention provides an introducer that provides access to laryngeal anatomy for the introduction of an airway device in the laryngeal anatomy.

The invention provides an epiglottic engager on a laryngeal access device.

The invention contemplates an introducer embodied as a relatively stiff blade-like device that is curved in longitudinal section. In a preferred embodiment, the distal end of the introducer is adapted to center on the midline hyo-epiglottic ligament and engages under the hyoid bone for accurate positioning. Alternately, the introducer can comprise a laryngeal blade. The introducer includes a track extending from a location near a proximal handle to a location near a distal end of the introducer. A coupling or engaging mechanism is provided near the distal end of the laryngeal airway device for slidably coupling the device to the track of the introducer. The laryngeal airway device is advanced along the track, which guides the sealing member to the laryngeal opening. At this point, the coupling mechanism disengages from the track and the introducer may be withdrawn, leaving the laryngeal airway device seated in its correct position for operation.

An alternate embodiment of the introducer includes a laryngeal scope blade having a posterior surface with a track.

An auxiliary feature to the introducer is an epiglottic engager that captures the epiglottis during airway introduction.

BRIEF DESCRIPTION OF THE DRAWING

FIG. 4 is a perspective view of a preferred embodiment of an introducer according to this invention.

FIG. 5 is a side elevation view of the laryngeal airway device of FIG. 1 coupled to the introducer of FIG. 4.

DETAILED DESCRIPTION OF THE PREFERRED EMBODIMENTS

A laryngeal airway device is designed to form a fluid seal against and within the rim of the laryngeal opening. Because the seal is against and within the rim of the larynx itself, and not with the pharyngeal structures surrounding the larynx, introduction of the device must be very accurate. The invention provides for guidance of a laryngeal airway device to its sealing position against the larynx. It should be noted however that the mechanisms and techniques that track or guide the laryngeal airway device to the laryngeal inlet could also work well with other airway devices, including a pharyngeal airway device. Therefore, although the following description is directed to a laryngeal airway device, this is not intended to so limit the application of the invention.

Figure 1:
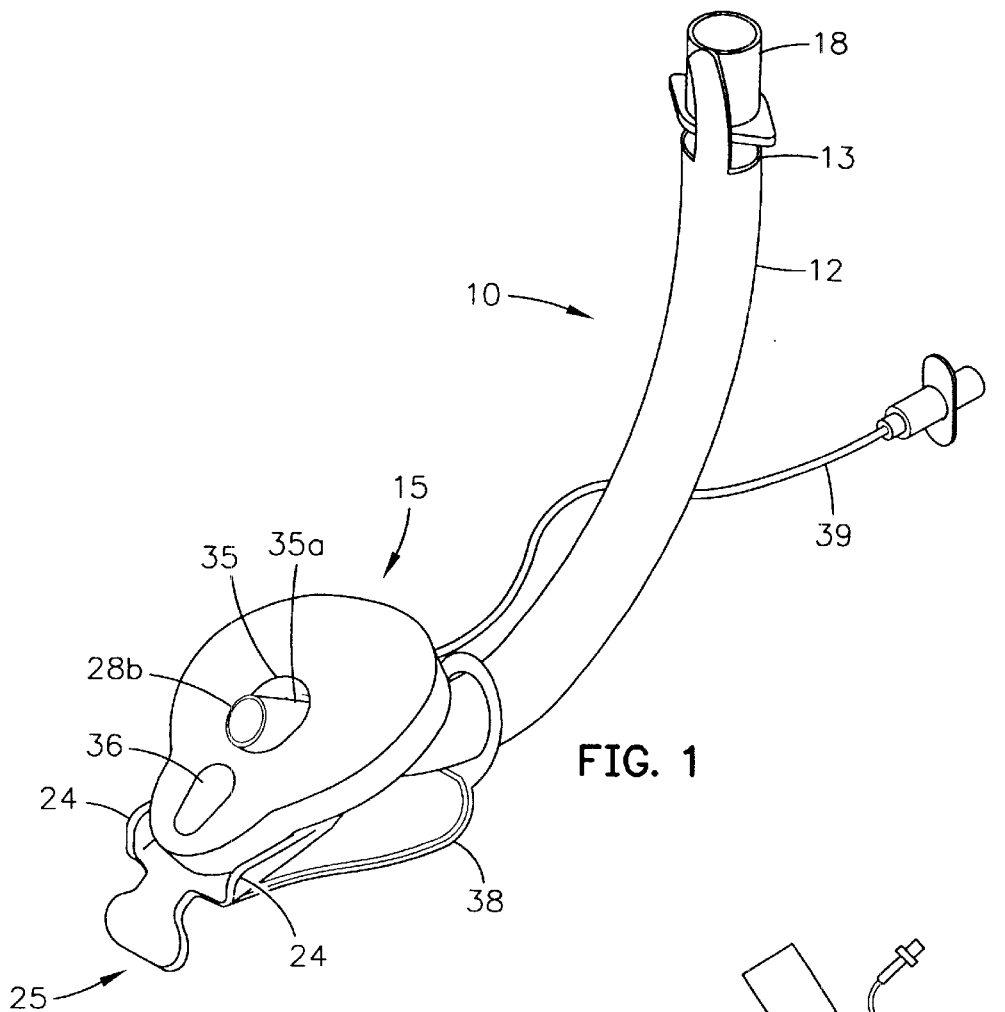
FIG. 1 is a perspective view of a laryngeal airway device having a coupler for engaging an introducer according to this invention.
Figure 3:
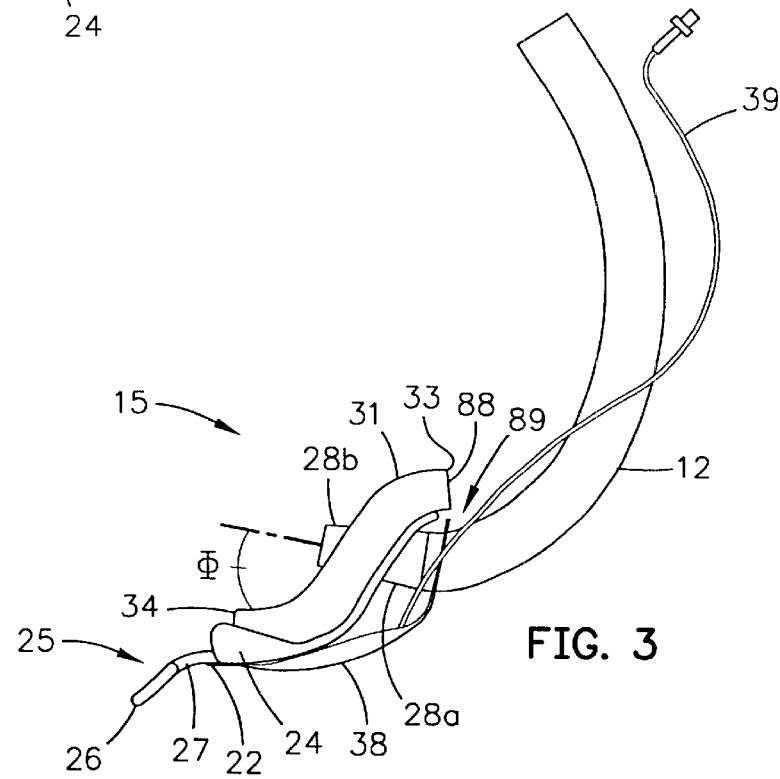
FIG. 3 is a side elevation view of the laryngeal airway device of FIG. 1.
Figure 2:
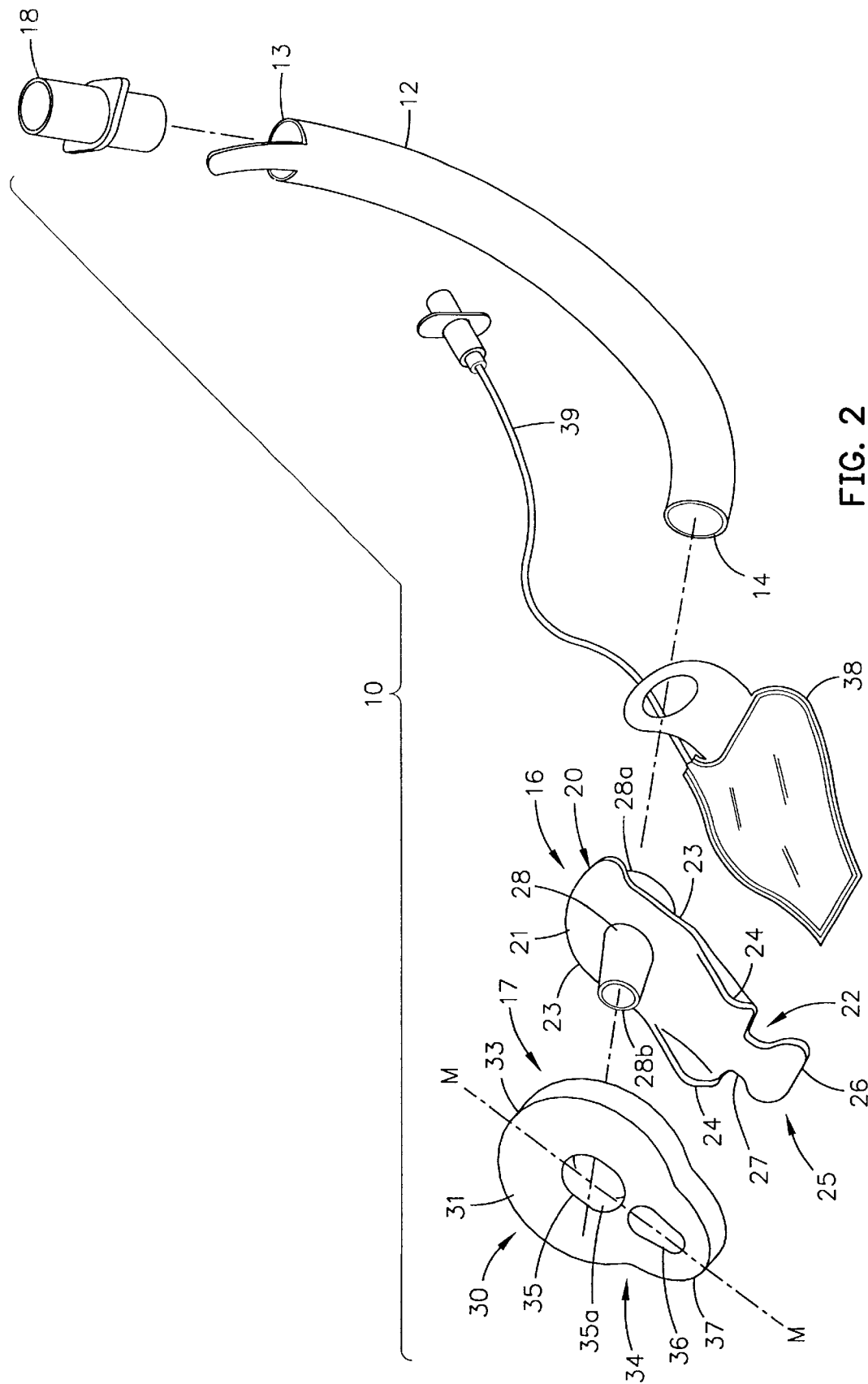
FIG. 2 is an exploded view of the laryngeal airway device of FIG. 1.
Figure 7:
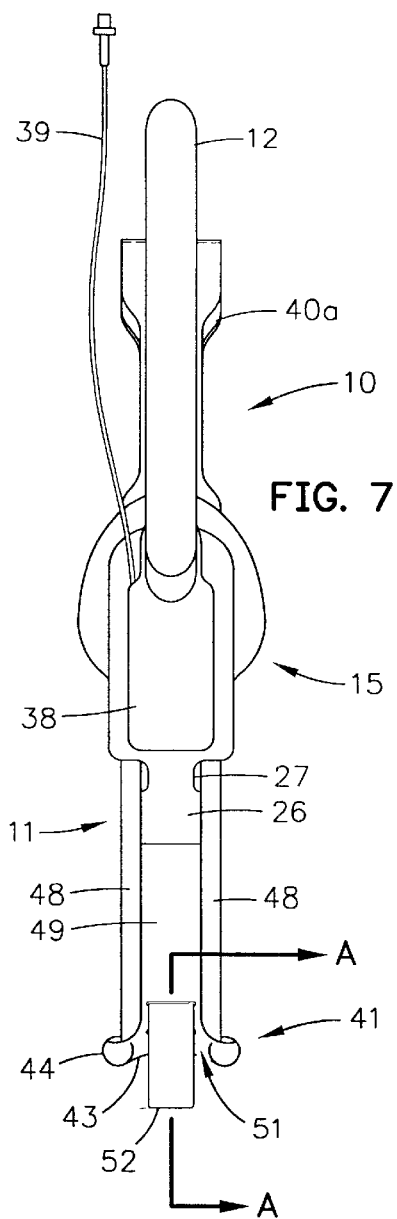
FIG. 7 is a plan view of the posterior side of the laryngeal airway device of FIG. 1 coupled to the introducer of FIG. 4.
Figure 6:
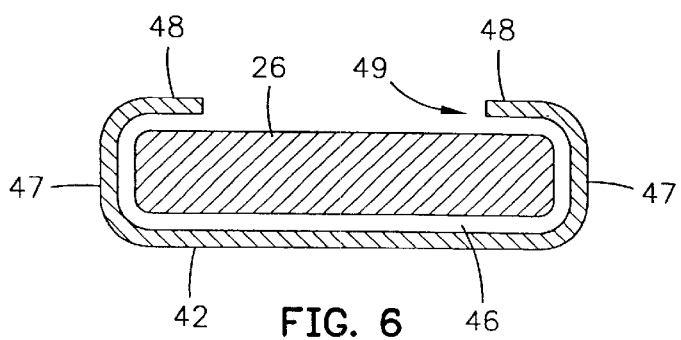
FIG. 6 is a sectional drawing taken along line 6—6 of FIG. 5.

FIGS. 1, 2 and 3 illustrate an example of a laryngeal airway device 10 that incorporates a feature of our invention. The laryngeal airway device 10 includes a flexible air tube 12 having first (proximal) and second (distal) ends 13 and 14, respectively. Preferably the tube 12 has a curved shape that conforms to the contour of the back of the tongue. A connector 18 is attached to the proximal end 13 to connect the tube to a ventilating means, which is not shown. A sealing member 15 is attached to the tube 12 near its distal end 14. The sealing member 15 includes a support member 16 and a compressible foam pad 17.

In more detail, the support member 16 has an upper (proximal) edge 20 and an anterior support surface 21, a distal end 22, and sides 23. The anterior support surface 21 has a generally sigmoid shape in a longitudinal section. In a lateral section, the shape of the anterior support surface 21 is generally flat, although there may be some variation to accommodate design, manufacturing, or operational considerations. The lower (distal) third of anterior support surface 21 extends to the distal end 22. Laterally of the distal end 22 are a pair of opposing cricoid retainers embodied as lateral flanges 24 that rise upwardly along the sides 23 from the distal portion of the anterior support surface 21. A coupler or track-engaging mechanism is provided in the distal portion of the support member 16. In these figures, this mechanism is embodied as a flexible track-engaging flange 25 that extends forwardly of the distal end 22. The flexible track-engaging flange 25 may perform one, or two useful functions: esophageal tracking and coupling to an introducer. Both are described below. The structure of the flexible track-engaging flange 25 includes a tab 26 that is connected to the distal end 22 by a pedestal 27. The lateral extent of the tab 26 at its widest section is preferably less than the width of the distal end 22 of the support member 16. The pedestal 27 is narrower than both the tab 26 and the distal end 22. The air tube 12 is enabled to project through the anterior support surface 21 of the support member 16 by a tubular, "snout-like" extension 28 that is a hollow cylinder having proximal and distal ends 28a and 28b, respectively. The tubular extension 28 is fixed to the support member 16 and the distal end 14 of the air tube 12 is received and fixed in the proximal end 28a of the tubular extension 28. The tubular extension 28 has a generally conical-like shape, with the narrower radius found at the distal end 28b and the wider radius at the proximal end 28a. The tubular extension may also be entirely cylindrical, or partially tubular, resembling a hood. Manifestly, the tubular extension 28 may be a shaped, molded portion of the air tube 12, or a piece that is separate altogether from the air tube 12 but attached to the distal end 14. The tubular extension 28 may also be slit to allow passage of an endoctraceal tube.

The compressible pad 17 preferably has a pear-like shape with an upper, or proximal portion 30, an anterior surface 31, and a lower or distal portion 34. The upper portion 30 is relatively wider than the lower portion 34. The compressible pad has an anterior surface 31. The upper portion 30 includes a hole 35 defining a passageway 35a in the sealing member 15 that is centered in the upper portion 30 and on a longitudinal midline M of the pad 17. The hole 35 opens through the anterior surface 31 and the passageway 35a extends through the pad 17, aligned longitudinally with the distal end 14 of the air tube 12. The tubular extension 28 is disposed in the passageway 35a. A slot, elongated hole, notch, or depression 36 is provided in the anterior surface 31, preferably centered on the midline M, and positioned between the hole 35 and a distal end 37 of the compressible pad 17. The length of the compressible pad 17 that extends from a proximal end 33 to the distal end 37 is such that, when the pad 17 is joined to the support member 16, the distal end 37 of the pad is positioned between the lateral flanges 24, set back from the distal end 22. This leaves open a channel defined laterally between distal portions of the lateral flanges 24 and longitudinally between the distal end 37 of the compressible pad 17 and the distal end 22 of the support member.

Preferably, and for illustration and example only, the support member 16 is a flexible plastic part that may be fabricated by molding 85 durometer PVC material. In this case, the air tube 12 should be made of somewhat stiffer material, for example 90 durometer plastic. The anterior support surface 21 has the generally sigmoid shape described above. Alternate embodiments of the anterior support surface 21 may be substantially flat, convex, or concave in longitudinal section.

The compressible pad 17 is preferably made by molding a closed cell foam having a density of about seven pounds to make the pad soft and conformable. When the compressible pad 17 is integrated with the support member 16, its anterior surface 31 takes on the sigmoid shape of the support member's anterior support surface 21. That is, the anterior surface 31 has a sigmoid contour imposed on it in a longitudinal section, but is substantially flat in opposing lateral sections that extend from the midline M laterally to the sides of the pad 17.

The sealing member 15 may be fabricated by molding or die cutting the elements 16 and 17 and then combining them into a unitary structure by attaching the pad 17 to the anterior surface 21 of the support member 16 by gluing, heat bonding, or ultrasonic bonding, by some form of riveting, by a combination of any of these methods, or by any other equivalent that will yield an integrated, unitary structure in which the foam pad 17 has a soft, compressible characteristic, while the support member 16 is relatively more rigid than the pad 17, yet with a flexibility in one or more of its elements that allows bending during use.

Although the sealing member 15 is illustrated and described as comprising two parts, it should also be evident that, with a selection of materials and methods, this member can comprise one part with two portions in which the materials and structures of one portion transition continuously or abruptly to the materials and structures of the other portion.

As is best seen in FIG. 3, an inflatable balloon 38 is disposed on the posterior side of the support member 16, extending generally between the proximal end 28a of the tubular extension 28 and the distal end 22 of the support member 15. A small tube 39 is provided for inflating the balloon 38. The balloon 38 may be provided to compensate for unusual variations in airway anatomy. It will not be necessary to inflate the balloon 38 in all patients in order to effect an airway seal.

Refer now to FIGS. 4, 5, 6 and 7 for an understanding of a preferred embodiment of an introducer with which the laryngeal airway device of FIGS. 1–3 is used. The introducer, indicated by generally 11, is a relatively stiff plastic or metal blade-like device having a straight portion and a curved portion. Preferably, though not necessarily the shape may be that of a capital "J". A first (proximal) end 40 of the introducer 11 transitions to a generally elongate proximal section with an anterior surface 42 and a posterior side 45. A handle 40a is provided at the proximal end 40. A second (distal) end 41 terminates the sharp "hook-shaped" portion of the "J"-shape of the introducer. Preferably, the introducer 11 is substantially flattened in cross-section. Preferably, although not necessarily, the distal end 41 preferably includes an indentation 43 on either side of which is a rounded protuberance 44. The indentation 43 is designed to accommodate the midline hyo-epiglottic ligament, while the protuberances 44 are designed to engage under the hyoid bone for accurate positioning of the introducer 11. These means of positioning have been described in U.S. Pat. Nos. 4,832,020 and 5,042,469, which are owned by the assignee and incorporated by this reference.

Figure 9A:
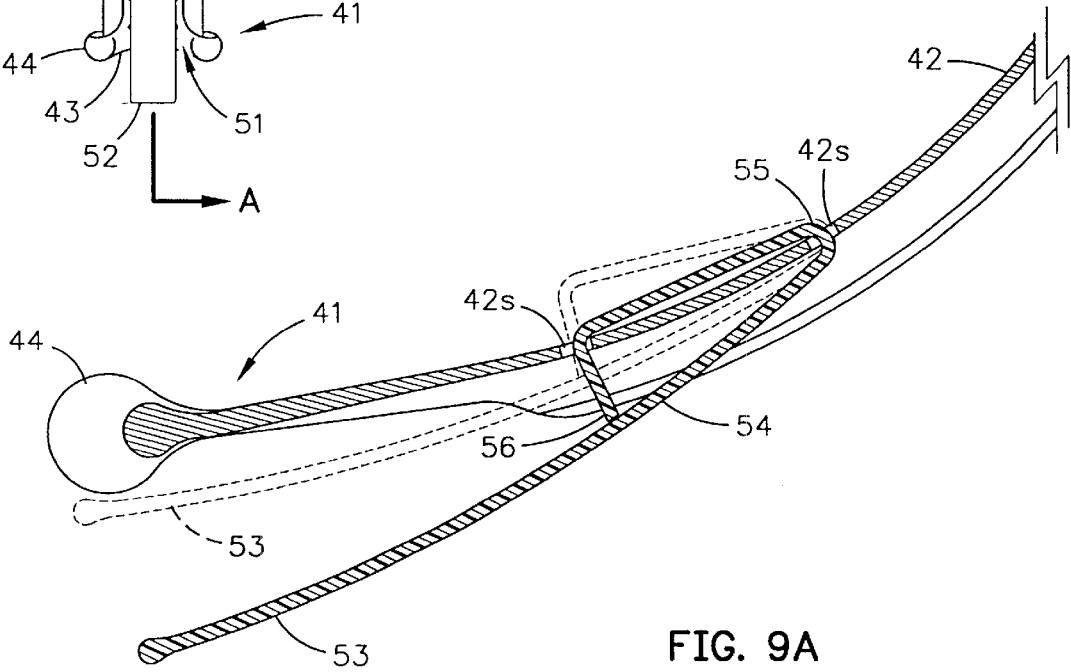
FIG. 9A is a magnified side sectional view of the distal end of the introducer taken along line 9—9 of FIG. 7 showing a pivotal epiglottic engager.

Referring to FIGS. 4, 5, 7, and 9A, an epiglottic engager, disposed on the distal end 41 of the introducer 11 is shown. Preferably this is a moveable epiglottic engager 52 pivotally attached to the distal end 41 of the introducer 11. As best seen in FIG. 9A, the epiglottic engager 52 has an elongate flattened forward section 53 that transitions to a closed triangular section 54 with an apex 55 and an opposing base 56. The apex 55 and base 56 are received in slots 42s through the posterior side 45 near the distal end 41 of the introducer 11. The forward section 53 projects beyond the base 56 toward the distal end 41 of the introducer 11. As best seen in FIG. 9A, the moveable epiglottic engager 52 can pivot between a fully extended position indicated by the solid lines and a closed position indicted by the dashed lines.

Figure 9B:
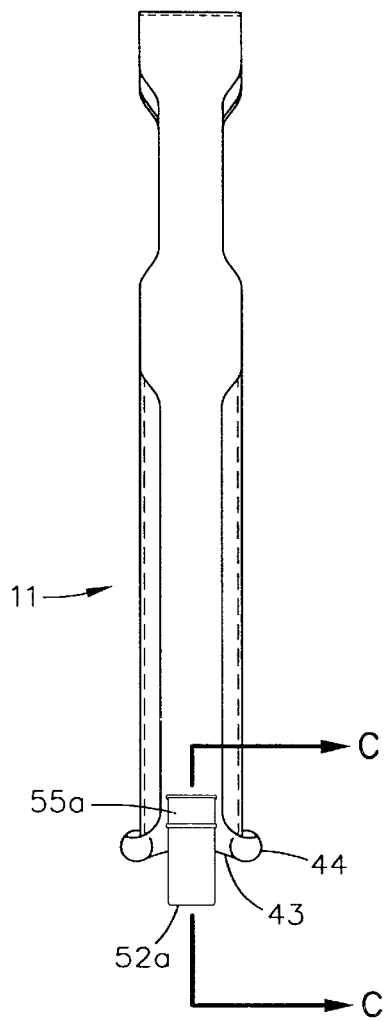
FIG. 9B shows an alternate embodiment of an epiglottic engager in a plan view of the posterior side of the introducer of FIG. 4.
Figure 9C:
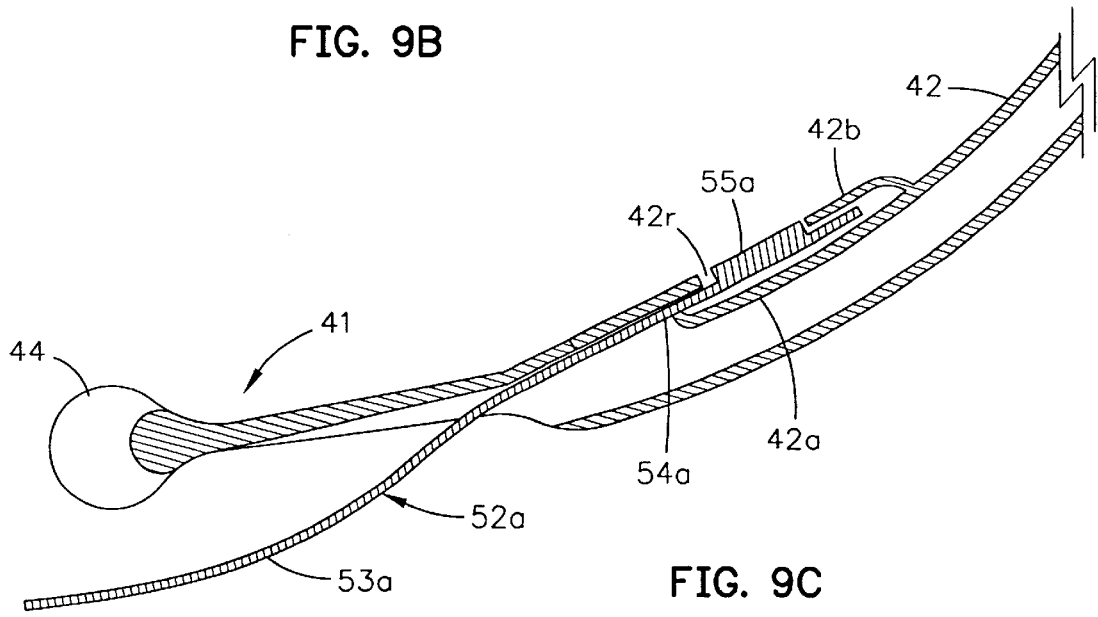
FIG. 9C is a magnified side sectional view of the distal end of the introducer taken along line 9C—9C of FIG. 9B.

FIGS. 9B and 9C illustrate an alternate embodiment epiglottic engager that is flexible and somewhat moveable, but not pivotable. As shown in these figures, the alternate embodiment epligottic engager 52a has an elongate flattened forward section 53a that transitions to a rear section 54a that includes a raised rectangular section 55a. In the distal region of the introducer 11, the anterior surface 42 has a first, lower extension 42a over or apart from which is a raised section 42b having a rectangular cutout 42r whose length and width are slightly greater than the corresponding dimensions of the raised rectangular section 55a. A space is formed between the lower section 42a and the upper section 42b within which the rear section 54a of the epiglottic engager 52a is received, with the raised rectangular section 55a being received in the rectangular cutout 42r. The forward section 53a projects forwardly form the rear section 54a, toward the distal end 41 of the introducer 11. While the alternate embodiment epiglottic engager 52a is not pivotable, it is flexible toward and away from the distal end 41.

Preferably either epiglottic engager is made of the same material as the blade. However, it is contemplated and may be desirable, that the engager be a different material, such as plastic. It should also be understood that the engager could be a removable component to accommodate substitution of differently dimensioned engagers.

FIGS. 1, 5, 6 and 7 illustrate elements of the device 10 and the introducer 11 that permit these two elements to operate cooperatively in solving the problem of tracking or guiding the device 10 into alignment with the laryngeal opening. The flexible track-engaging flange 25 on the distal end 22 of the sealing member 15 couples to a track 46 formed on the posterior side of the introducer 11. As shown best in FIGS. 5–7, the track 46 includes two opposing slide rails that are generally "U"-shaped and are formed by upwardly-extending wall portions 47, which extend longitudinally on the posterior side 45. The wall portions 47 transition to medially-extending sections 48. There is a gap 49 between the medially-extending sections 48.

The device 10 is coupled to the introducer 11 by orienting the compressible anterior surface 31 of the sealing mechanism toward the posterior side of the introducer 11 and inserting the flange 25 between the "U"-shaped slide rails on the posterior side of the introducer 11 where the rails begin at 50 near the proximal end 40. The opening 49 captures the edges of pedestal 27, while the tab 26 of the flange 25 is retained between the slide rails. When the device is pushed toward the distal end 41 of the introducer 11, the air tube 12 is rotated to place the distal end 28b of the tubular extension 28 toward the posterior side, within the opening 49 between the slide rails. When pressure directed toward the sealing member 15 is applied on the tube 12, the device is advanced, sealing member 15 first, along the posterior side of the introducer 11 towards its distal end 41. When the flange 25 emerges from between the slide rails at the opening 51 where the medially-facing portions 48 of the slide rails taper toward the vertical portions 47, the flange 25 is released from the rail track of the introducer 11 and the device 10 is uncoupled from the introducer 11.

Figure 8:
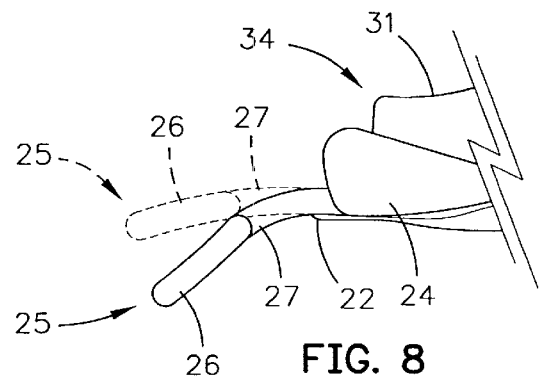
FIG. 8 is a magnified side view of a portion of the distal end of the laryngeal airway device of FIG. 1.

In this exemplary construction of the device 10, and as illustrated in FIG. 8, the material of which the support member 16 is made imparts a flexibility that permits the flange 25 to rotate between a first position indicated by the solid lines in FIG. 8 and a second position that is indicated by the dashed line in FIG. 8. In the first position, the device 10 is not coupled to the introducer 11. However, in the second position, the flange 25 has been engaged between the slide rails of the introducer 11 and the device 10 has been advanced to the point just before the flange 25 is released.

Positioning of the Laryngeal Airway Device

Figure 10A:
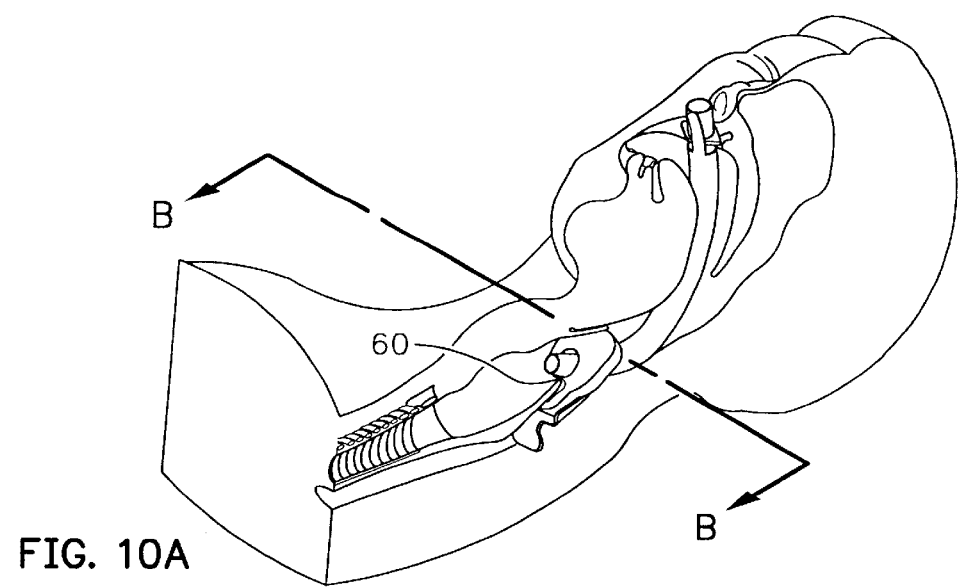
FIG. 10A is a partial cutaway perspective view of the anatomy of the throat with the laryngeal airway device of FIG. 1 positioned in the anatomy.

FIG. 10A is a cutaway perspective view of the anatomy of a throat with the laryngeal airway device 10 seated against the laryngeal opening 60. This figure and FIG. 10B are provided for an explanation of how the laryngeal airway device is positioned and retained in the throat, although these functions of the device are not necessary to the practice of this invention.

Figure 10B:
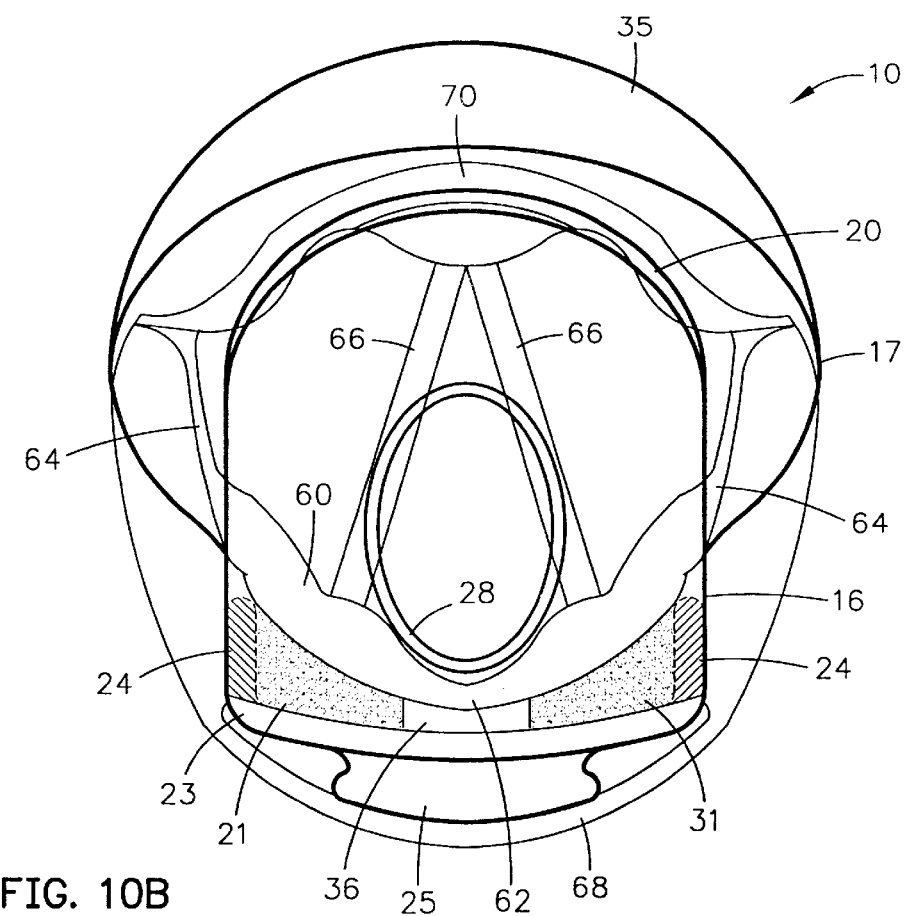
FIG. 10B is a schematic lateral cross-sectional representation of the anatomy of the throat taken along line B—B of FIG. 10A.

FIG. 10B is a schematic lateral cross-sectional representation of the laryngeal anatomy taken along line B—B of FIG. 10A. The direction of the view is toward the throat, from behind the sealing member 15. The view is schematic and imaginary, assuming that the sealing member is substantially transparent, with the outlines of its major components—the support member 16 and the compressible pad 17—indicated by heavy lines. In these views, the rim of the laryngeal opening is indicated by reference numeral 60, the inter arytenoid notch by reference numeral 62, the aryepiglottic folds by 64, the vocal chords by 66, the esophagus by 68, and the epiglottis by 70.

With respect to lateral positioning, the two opposing, substantially parallel lateral flanges 24 extend anteriorly and seat on each side of the cricoid cartilage which is disposed toward the bottom of the larynx, distal to the rim 60. When the cricoid cartilage is cradled between the lateral flanges 24, it is contained within the channel defined between the distal portions of by these elements, which assures lateral alignment of the tubular extension 28 within the laryngeal opening with respect to the vocal chords 66. FIGS. 1, 2, and 3 illustrate the lateral flanges 24 as being located on the lateral edges 23 of the anterior supporting surface 21. In this illustration, the lateral flanges 24 extend for only part of the length of the sides; however, they may extend for shorter, or longer distances along the sides. In a side elevation view, the ridges may assume many shapes including, but not limited to, wall-like, rounded, square or rectangular, triangular, truncated triangular, or a combination of these shapes or any shapes that are equivalent and that serves the purpose of lateral retention. When viewed elevationally from the front of the support member 16, the lateral flanges 24 may have many shapes including, but not limited to, a wall, a tab, or a cylinder.

In considering cephalad-caudad positioning, refer to FIGS. 1, 3, and 10. Recall the sigmoid shape of the anterior support surface 21, which is imposed on the anterior surface 31 of the compressible pad 17. The lower portion of the sigmoid that is described by the lower or distal portion 34 of the compressible pad is designed to seat between the larynx and the posterior pharynx, stabilizing the device 10. The lower portion of the support member 16, that is, the portion generally just above the distal end 22 to the end of the flange 25, is preferably angled posteriorly when molded. The posterior angle assures that the flange 25 and distal end 22 will be applied directly against the posterior wall of the pharynx when the airway 10 is advanced into its position of use. The midportion of the sigmoid shape is angled to abut the angled rim of the laryngeal opening 60, along the ary-epiglottic folds. The upper portion of the sigmoid shape is flattened to seal against the posterior side of the epiglottis, within the laryngeal opening. The "snout-like" tubular extension 28 protrudes through the hole 35, beyond the anterior surface 31, into the laryngeal opening 60. This snout helps create a fluid seal against the larynx by holding the laryngeal tissues out of the distal opening 28b, to prevent obstruction of air flow. As stated above, the tubular extension 28 is preferably shaped like a truncated cone, with its wide base attached to the distal end 14 of the air tube 12. The narrow distal end 28b is opened to allow air flow and it is this part that penetrates most deeply into the laryngeal opening 60.

Accurate cephalad-caudad depth placement is provided by the combination of the "snout-like" distal end 28b of the tubular extension 28 and the lower part 34 of the anterior surface 31 of the sealing member. This combination creates a "hook". The angle Φ (FIG. 3) between the distal end 28b of the tubular extension 28 and the lower anterior surface portion 34 is preferably an acute angle, greater than 0° and less than 90°. The base of the notch 62 formed between the arytenoid cartilages is made of the arytenoidous muscle overlaying the cricoid cartilage. These structures are very firm and assure a positive end-point when contacted with a longitudinal force. The hook described by the acute angle Φ is designed to catch on the cartilage and muscle between the arytenoid cartilages, on the posterior edge of the laryngeal opening. With reference to the "cut pipe" analogy described above, the hook described by the angle Φ engages over the posterior rim of the laryngeal opening, which is the obtuse angled edge of the rim. With the distal end 28b of the tubular extension 28 lodged inside the laryngeal opening, the hook cannot slip out distally or become displaced laterally when longitudinal pressure is applied to the airway. The arytenoid depression 36 and the anterior surface 31 assists in this positioning by receiving small corniculate tubercles that are on the posterior side of the larynx and that are near the arytenoid notch. The tubercles are received in the depression 36, and assist in positioning the laryngeal airway device 10 longitudinally in the laryngeal opening.

Referring once again to FIGS. 10A and 10B, the cephalad-caudad positioning of the laryngeal airway device 10 may be understood. As shown in this figure, the inter arytenoid notch 62 is positioned between the tubular extension 28 and the distal portion 34 of the compressible pad 17. Although not shown in this view, the distal end 28b of the tubular extension 28 is located above the vocal chords 66. In addition, the arytenoid depression 36 has received the forward portion of the inter arytenoid notch 62 that includes the corniculate tubercles. This provides space in which the tubercles can be received, which enables the posterior side of the inter arytenoid notch to relax somewhat and move with the bottom portion of the tubular extension 28.

Retention of the Laryngeal Airway Device

In FIG. 3, there is shown an edge surface 88 on the proximal edge 33 of the compressible pad 17 and a surface 89 that extends from the proximal end 28a of the tubular extension 28 across the distal end 14 of the tube 12. The edge surface 88 and the tube surface 89 receive the tissues on the back portion of the tongue when the sealing member 15 has been advanced to seal against the laryngeal opening with lateral and depth positioning as described above. At this location, the back portion of the tongue relaxes, draping over the edge surface 88 of the proximal edge 33 and hanging down onto and around the surface 89. The rough texture of the surface of the tongue prevents the compressible material at the edge surface 88 from easily sliding across the surface of the tongue. This retains the airway in tight approximation with the larynx by anchoring it with the base of the tongue. The edge surface 88 that is presented by the structure of the distal portion of the laryngeal airway device 10 capitalizes on the flexibility of the tongue to capture the airway at the proximal edge 33 where the contact between the anchored base of the tongue and the edge surface 88 retains the edge 33 and prevents the airway 10 from being ejected from its correct positioning against the rim of the laryngeal opening.

Operation According to the Invention

The cooperative operations of the laryngeal airway device and the introducer will now be explained with reference to FIGS. 11–18.

Figure 11:
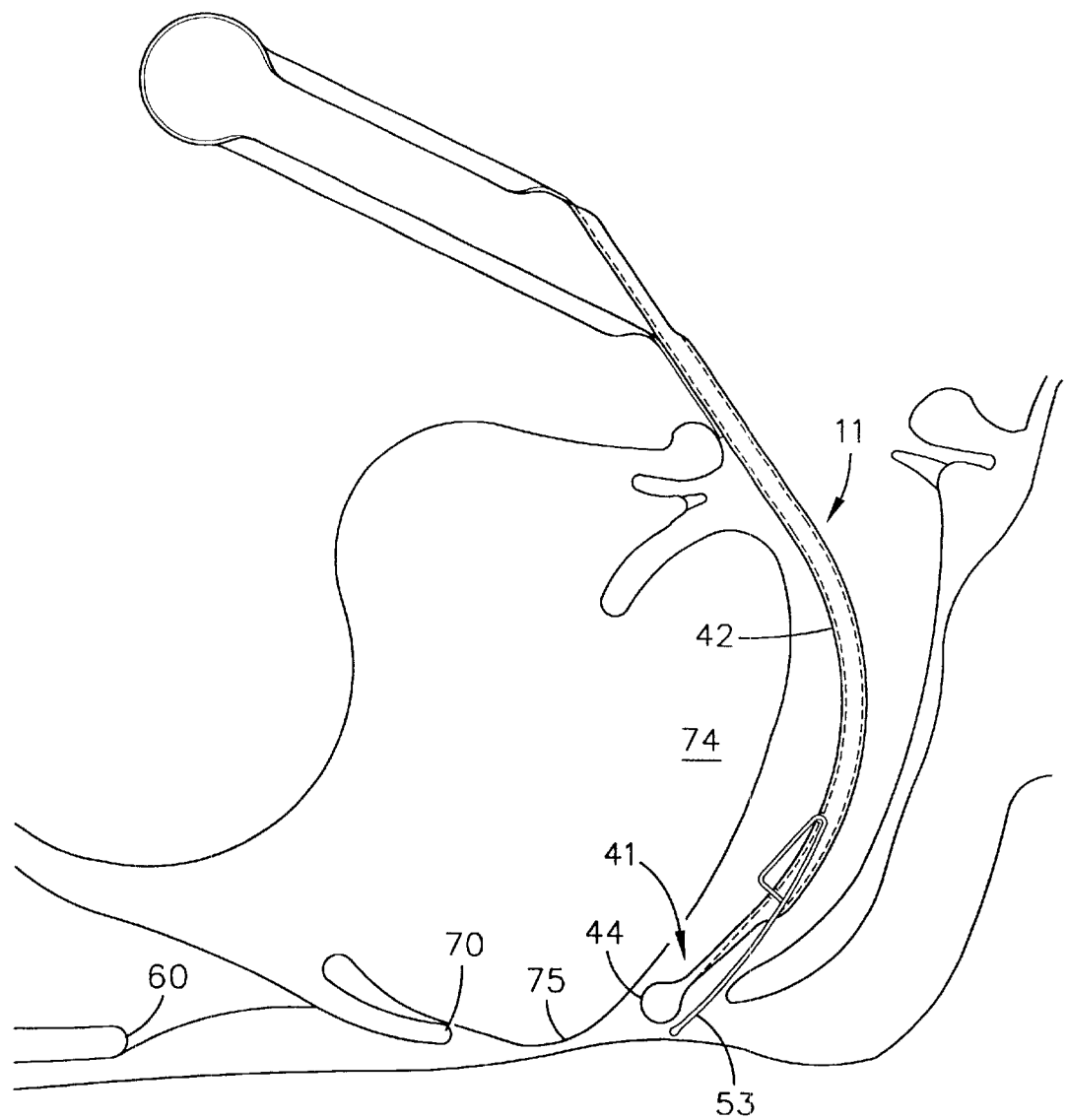
FIGS. 11–14 are schematic side cross-sectional representations of the anatomy of the throat showing the operation of the introducer of FIG. 4.
Figure 12:
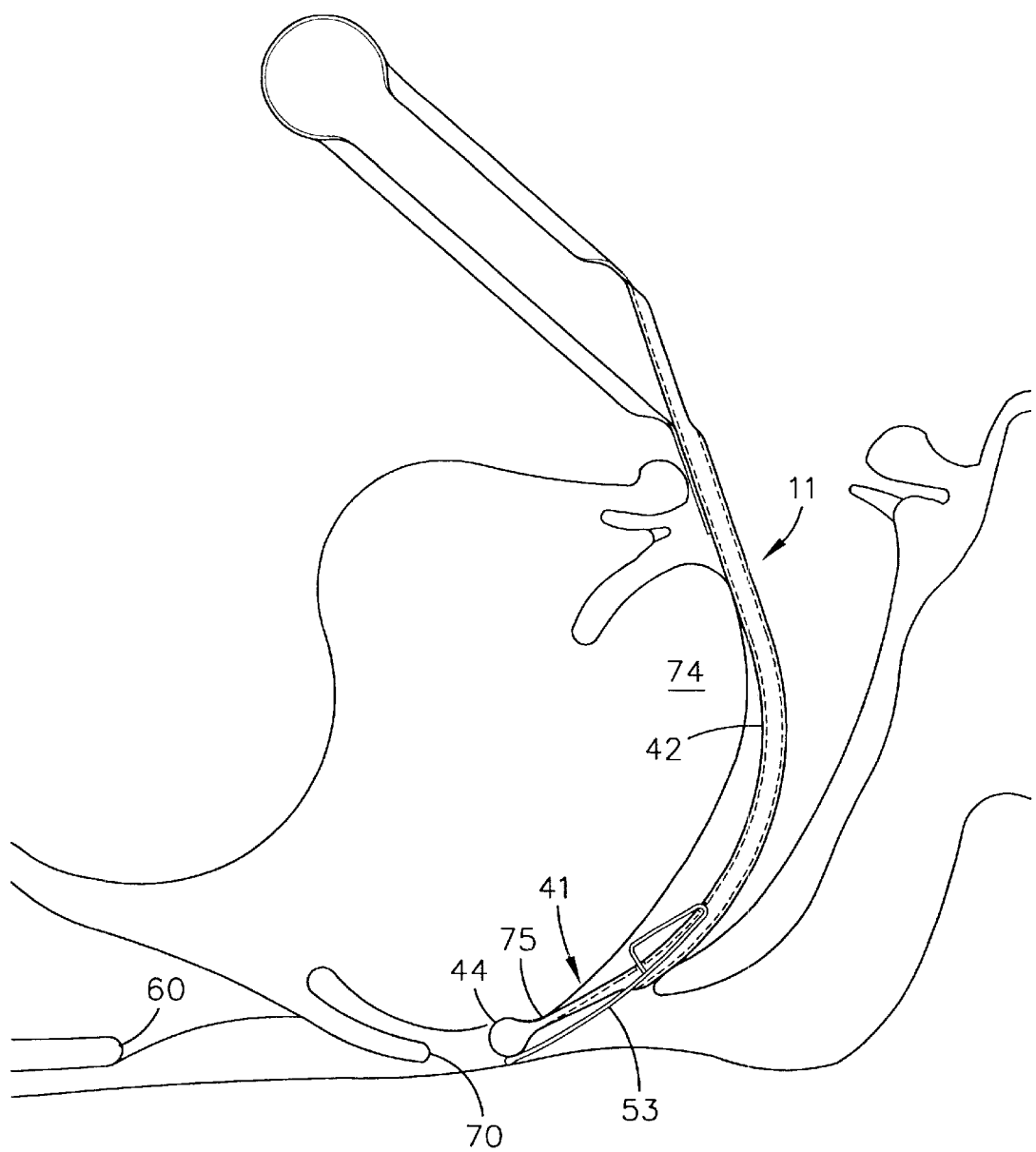
Figure 13:
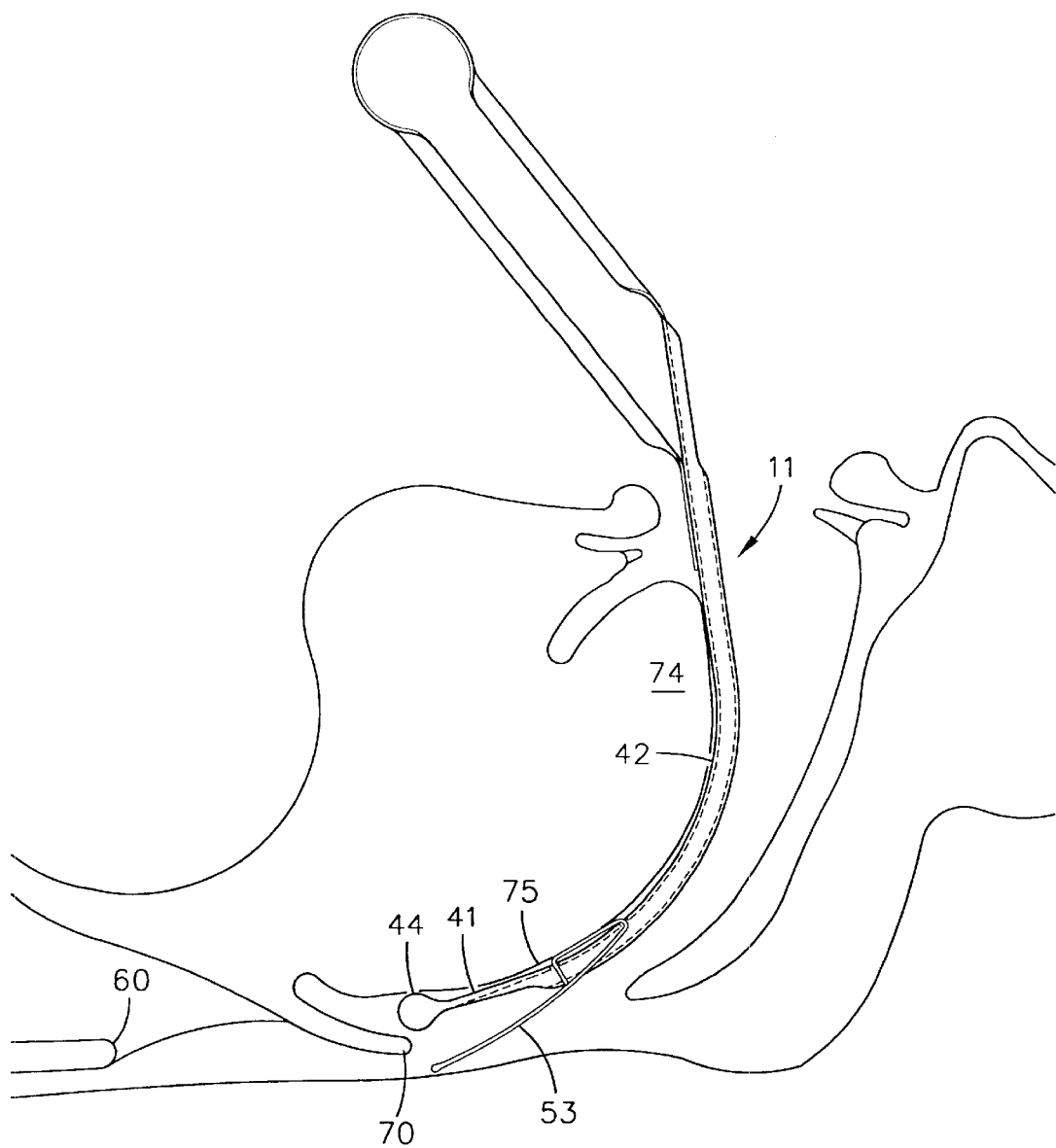
Figure 14:
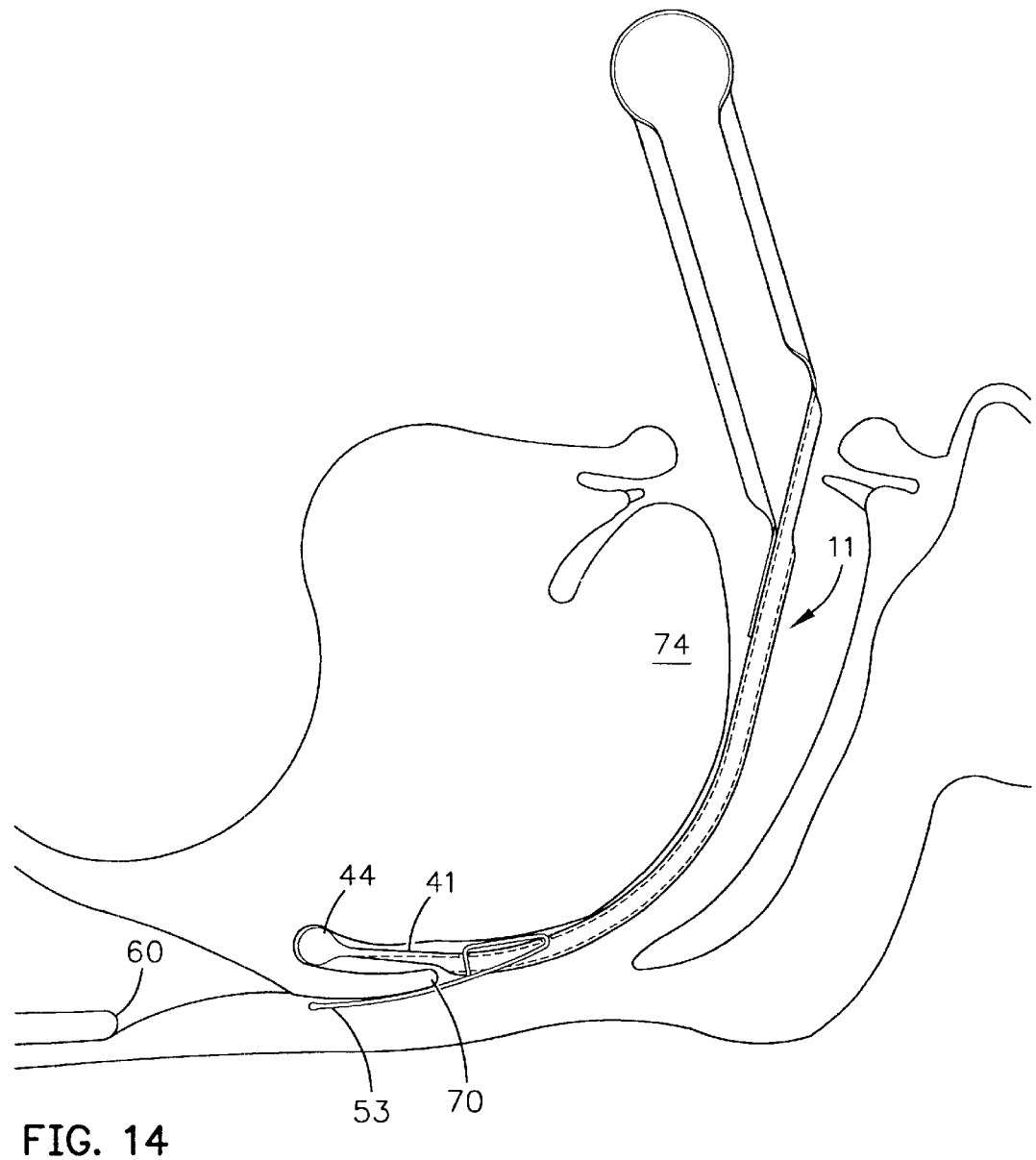
Figure 15:
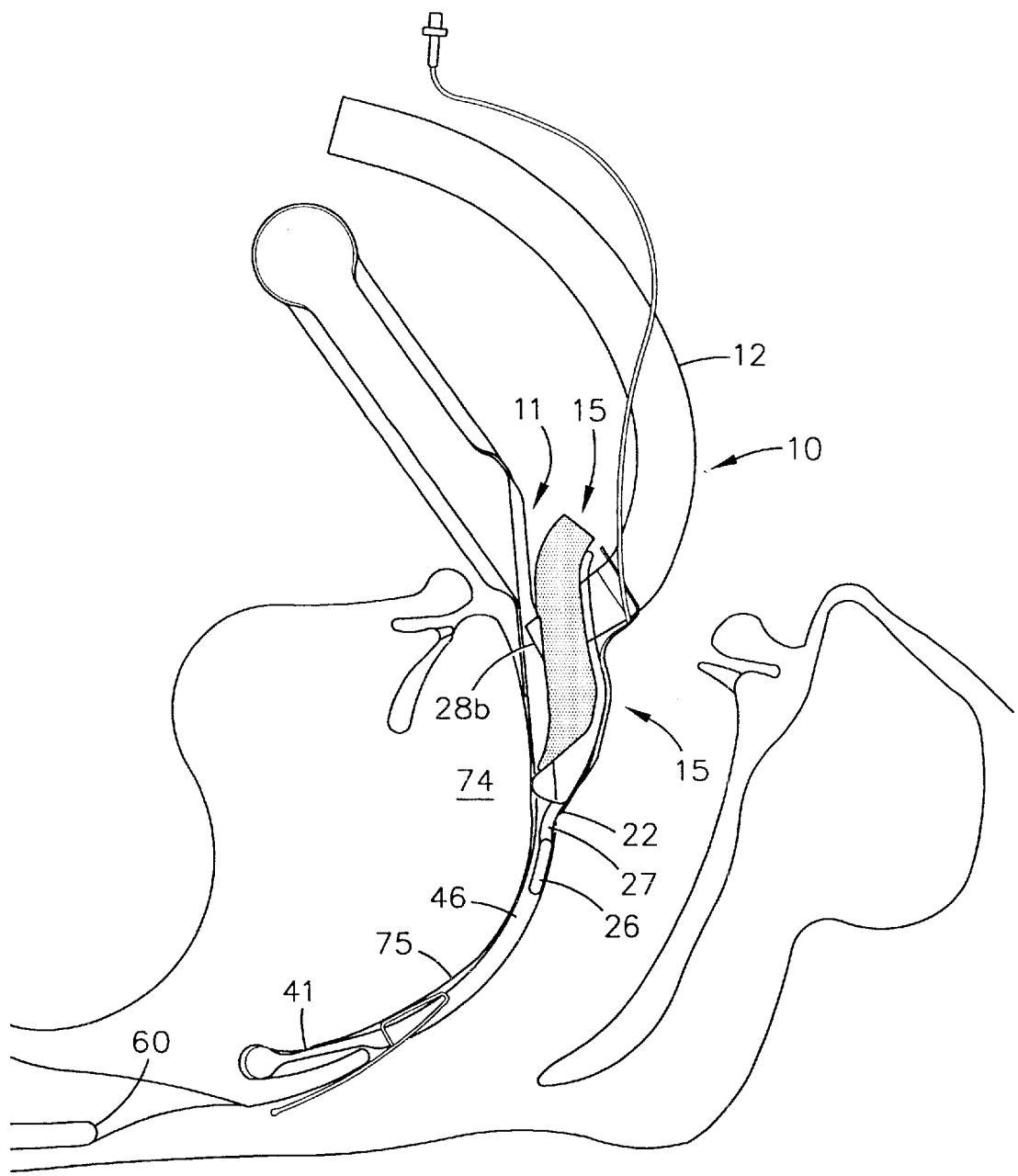
FIGS. 15–18 are schematic side cross-sectional representations of the anatomy of the throat showing the introduction and positioning of the laryngeal airway device of FIG. 1.
Figure 16:
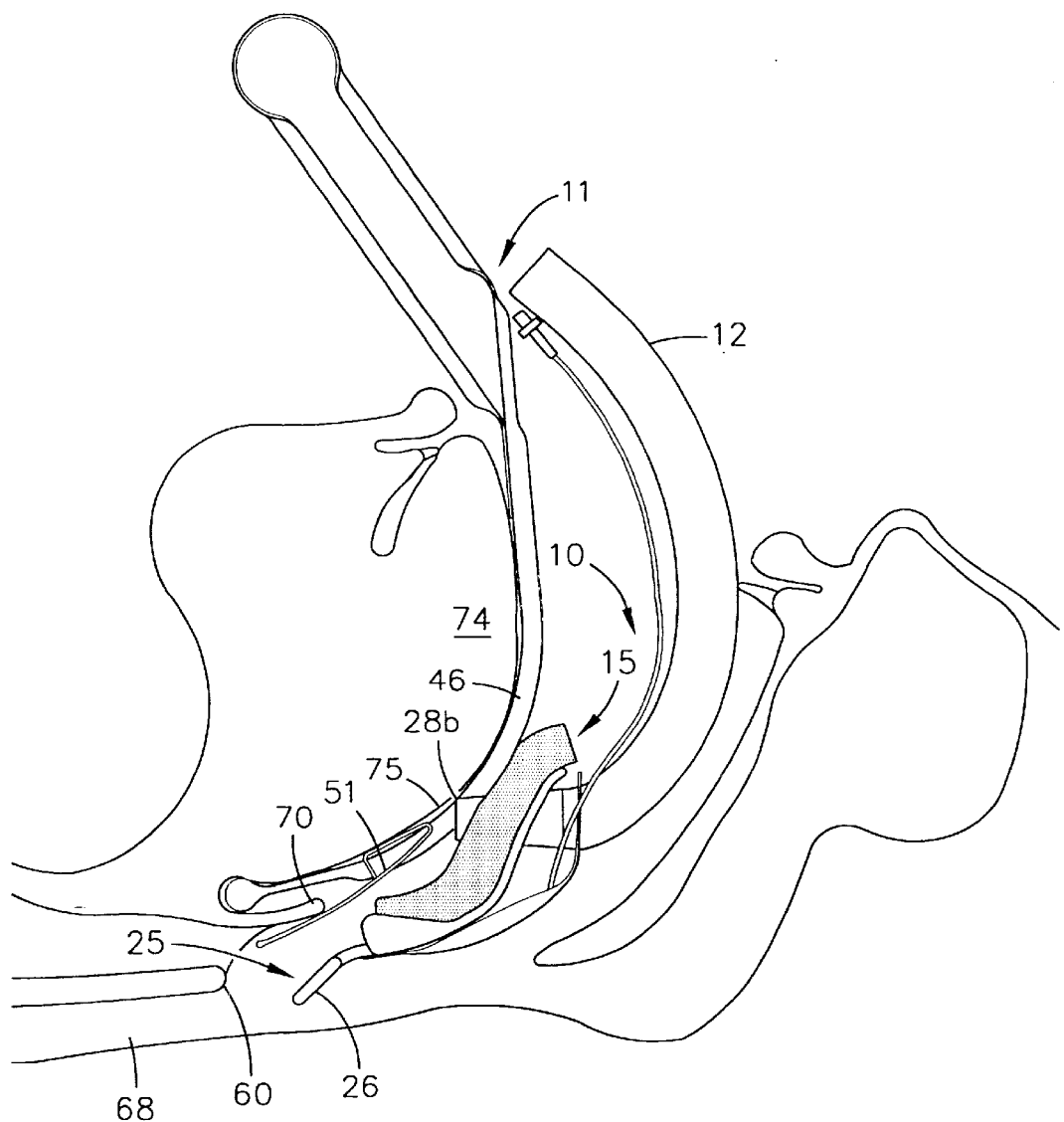
Figure 17:
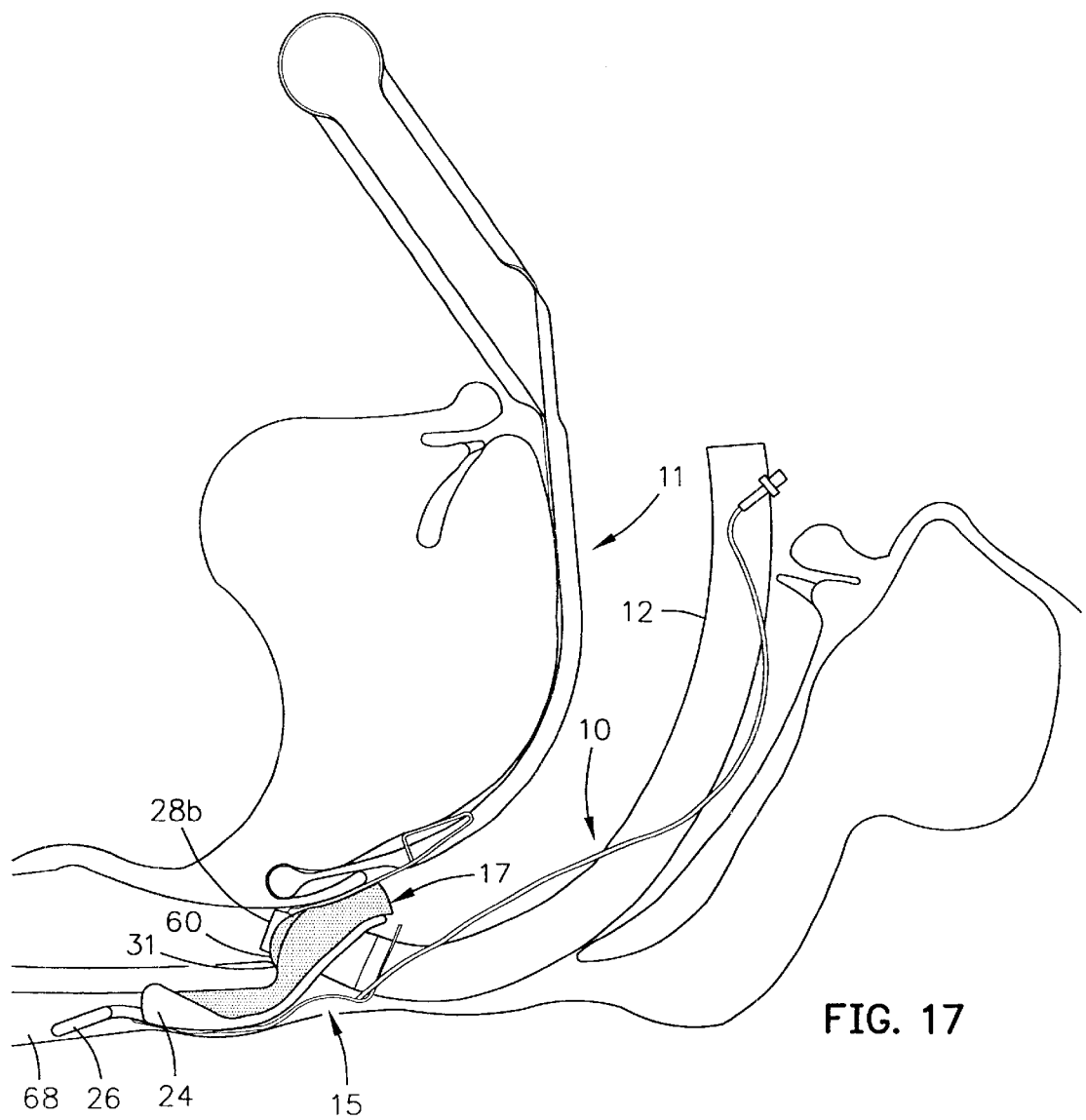
Figure 18:
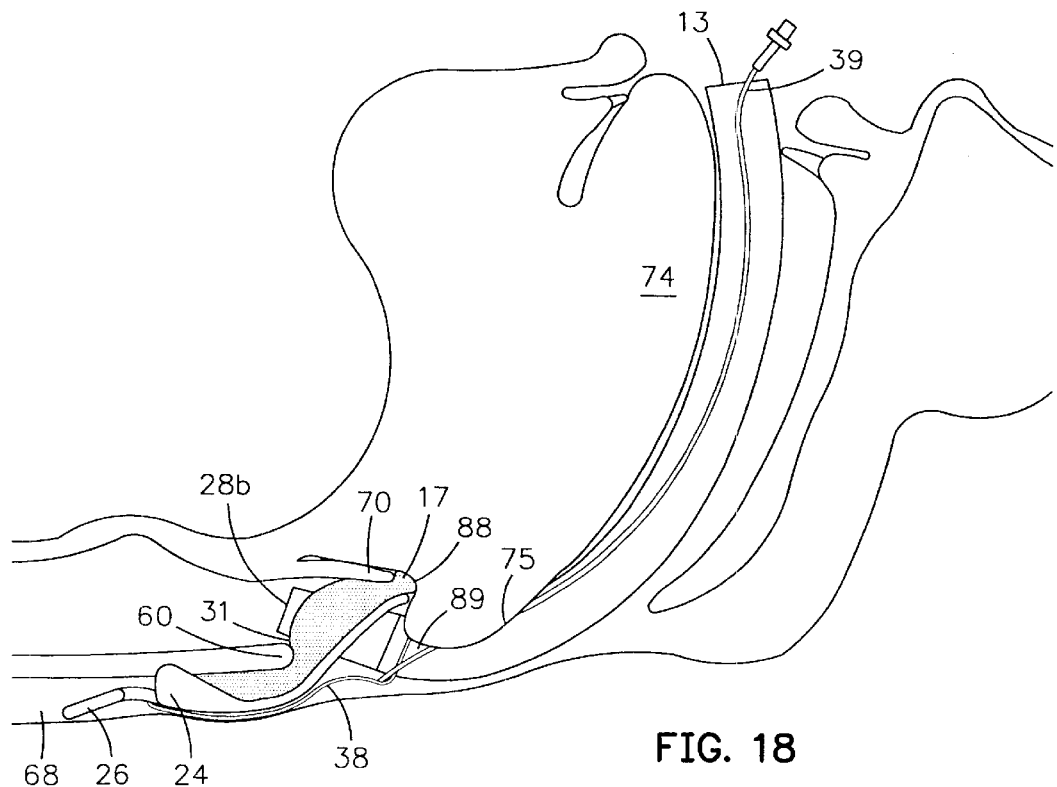

Initially, in FIG. 11, the introducer 11 is inserted, distal end 41 first, through the mouth, traversing the tongue 74 where, in FIG. 11, one of the rounded protuberances 44 is shown approaching the sharp curvature 75 at the back of the tongue. As the distal end of the introducer 11 advances, the flattened forward section 53 of the epiglottic engager 52 is rotated toward the posterior side 45 near the distal end 41 by contacting the back of the throat. In FIG. 12, as the distal end 41 of the introducer 11 passes the sharp curve 75 at the back of the tongue 74, the narrow dimensions of the throat force the structure of the distal end 41 against the back of the tongue 74, lifting the lower tissues of the tongue away from the epiglottis 70. At this point, the flattened forward section 53 of the epiglottic engager 52 is fully rotated toward the distal end 41, between the rounded protuberances 44. In FIG. 13, the introducer 11 is pulled upwardly as it is advanced into the throat, further raising the tissue at the base of the tongue 74 and widening the throat, allowing the flattened forward section 53 of the epiglottic engager 52 to pivot away from the distal end 41 toward the back of the throat. As the distal end 41 of the introducer 11 is advanced to the position shown in FIG. 14, the epiglottis 70 is trapped between the distal end of the introducer 11 and the flattened forward section 53 of the epiglottic engager 52. This retains the tip of the epiglottis 70 upwardly, keeping it out of the space in the throat through which the sealing member of the laryngeal airway device must pass. At this point, the indentation 43 of the distal end 41 of the introducer has received the hyo-epiglottic ligament, while the protuberances 44 have been engaged under the hyoid bone to position the introducer 11. In FIG. 15, the laryngeal airway device 10 has been coupled to the introducer 11, with the tab 26 engaged in the track 46. The sealing member 15 is oriented as described above. The laryngeal airway device 10 is advanced along the introducer 11 over the tongue toward the curve 75 at the back of the tongue 74. In FIG. 16, the laryngeal airway device 10 has been advanced to the point where the flange 25 has emerged from the opening 51 at the distal end of the track 46. As the distal end of the laryngeal airway device 10 is advanced further into the throat, the flange 25 springs back to its first position with the tab 26 angled posteriorly toward the back of the throat. At this position, it can perform esophageal tracking. Referring to FIGS. 17 and 18, as the laryngeal airway device 10 is advanced further into the throat, it eventually seats against the rim 60 of the laryngeal inlet, with the distal end 28b of the tubular extension 28 extending within the laryngeal inlet and the anterior surface 31 of the compressible pad 17 engaging and sealing against the rim 60, and extending partly into the laryngeal opening in the vicinity of the distal end 28b. At the same time, the distal end of the sealing member 15 has tracked down the back of the throat with the tab 26 of the flange 25 tracking toward the esophagus 68. At this point, the above-described features of the laryngeal airway device have aligned and positioned it laterally and along the depth axis of the larynx. Now, the introducer 11 is withdrawn, leaving the laryngeal airway device 10 seated. Withdrawal of the introducer causes the tongue to drape down over the edge surface 88 and the surface 89 which retains the laryngeal airway device in the manner described above.

Clinical experience has shown the inventors that optimal lateral positioning with the laryngeal airway device 10 can be accomplished with a specific maneuver. Once the device 10 is positioned, with the flange 25 located between the larynx and the posterior wall in the pharynx in the upper reaches of the esophagus 68, the proximal end 13 of the laryngeal airway device 10 is grasped. The laryngeal airway device 10 is pulled very slightly out of the mouth against the tension of the tongue and then pushed back in. This maneuver is known as the "Arnold maneuver". The device 10 is not pulled so far out as to cause disengagement with the epiglottis 70 but merely to partially disengage the anterior surface 31 from the rim 60 of the laryngeal inlet. When the device 10 includes the distal end 28b, the Arnold maneuver disengages the tip of the distal end 28b from an arytenoid cartilage that may be obstructing the opening 60. On reinsertion, the distal end 28b is unobstructed and lies within the laryngeal inlet 60. The Arnold maneuver in conjunction with a device 10 that includes the lateral flanges 24 or their equivalent has been shown to dependably orient the device 10 in the lateral dimension with respect to the larynx. If the device 10 includes the snout like distal end 28b, the Arnold maneuver dependably places the distal end 28b within the laryngeal inlet 60 and clears tissue that may obstruct airflow.

If necessary to achieve a desired level of positive pressure, the seal that the laryngeal airway device makes with the laryngeal inlet may be assisted by inflation of the balloon 38 through the tube 39. This may follow the Arnold maneuver, if indicated. Inflation of the balloon 38 will rotate the sealing member anteriorly with respect to the laryngeal opening, further tensioning the opening and further urging the anterior surface of the compressible pad into sealing engagement against the opening.

ALTERNATE EMBODIMENTS

Figure 19A:
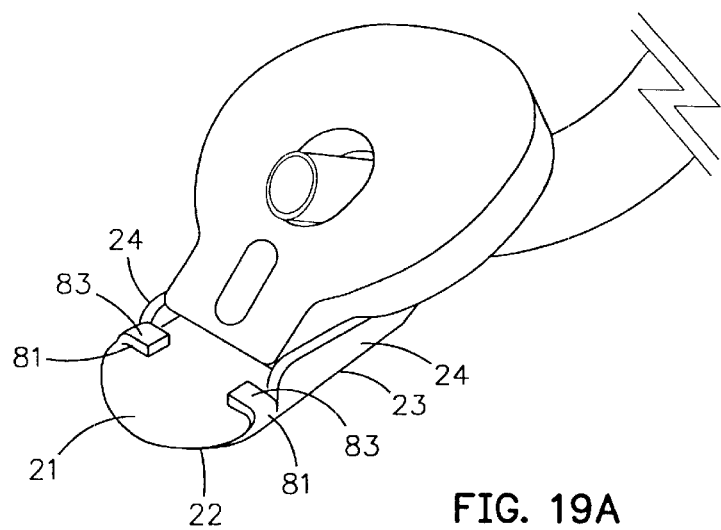
FIGS. 19A, 19B and 19C illustrate alternate embodiments of features of the laryngeal airway device coupler and the introducer track.
Figure 19B:
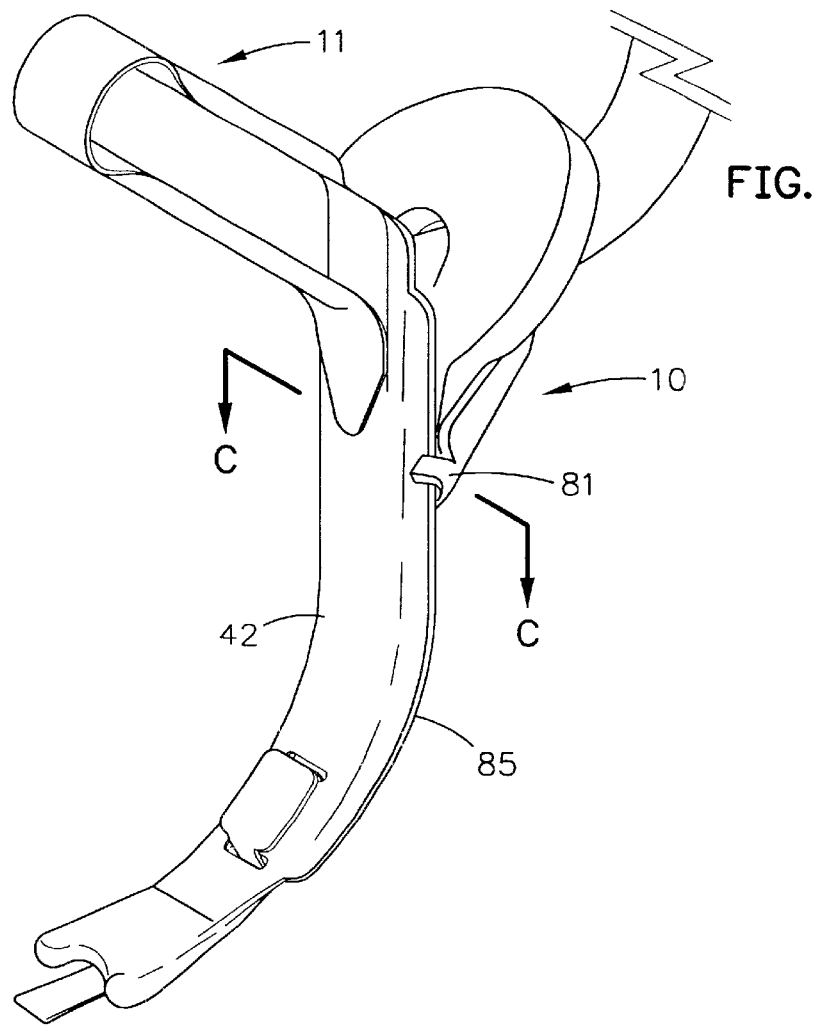
Figure 19C:
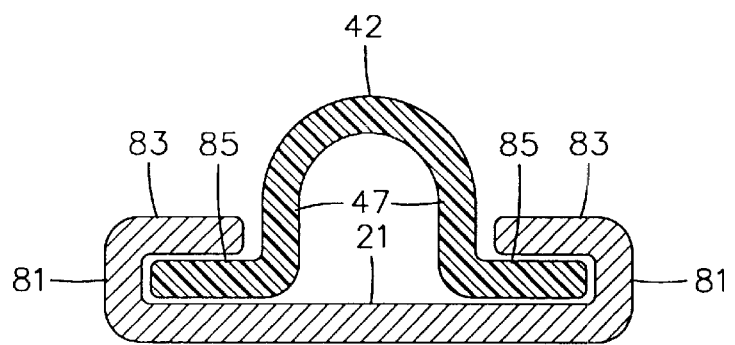
Figure 20A:
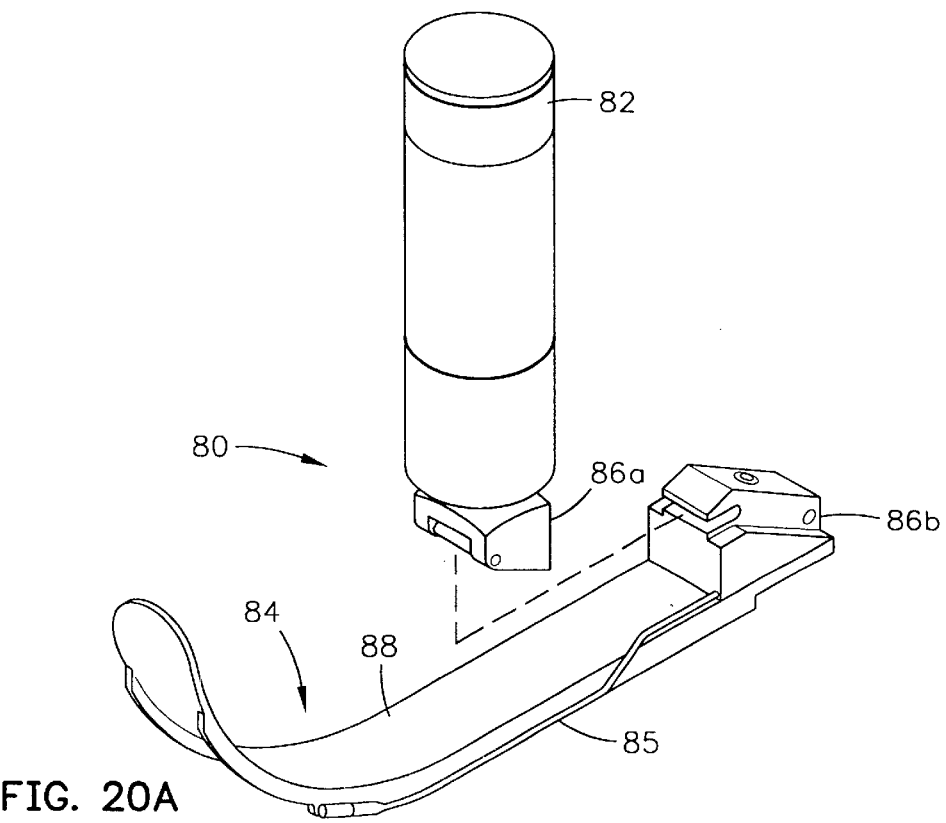
FIGS. 20A–20D show various views of an alternate embodiment of the introducer.
Figure 20B:
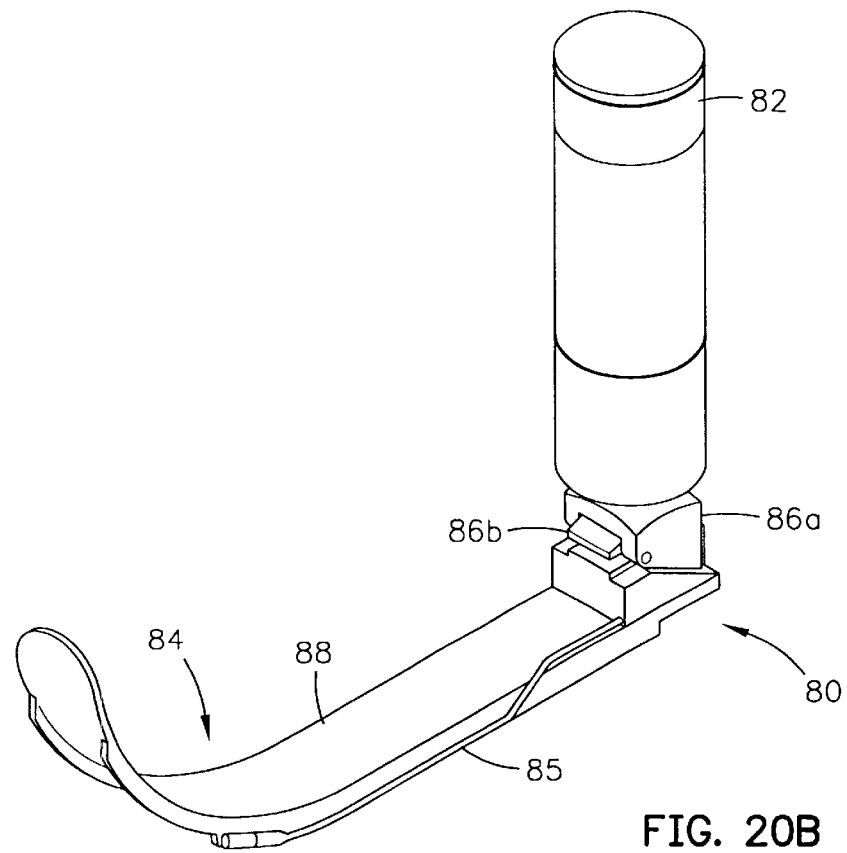
Figure 20C:
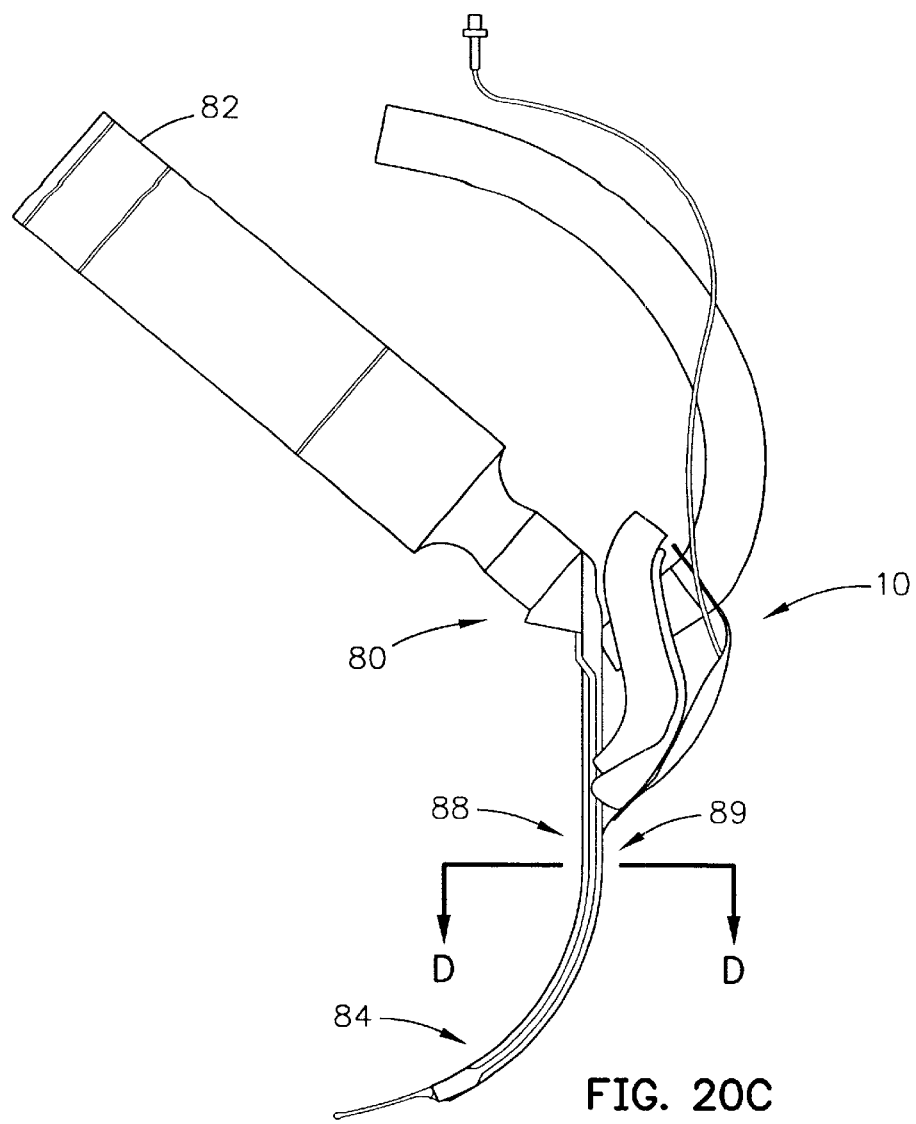
Figure 20D:
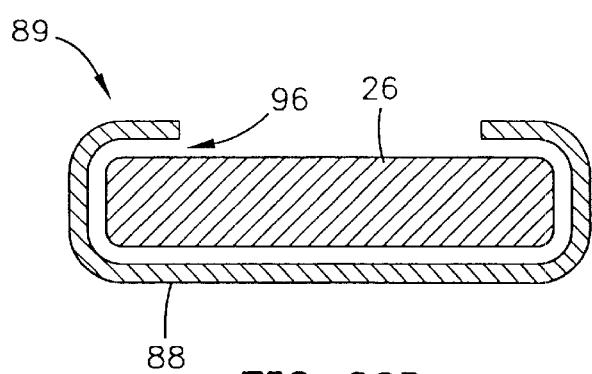

The tracking or guiding feature of this invention may be implemented in many ways. FIGS. 19A, 19B and 19C show an alternate embodiment of this feature. In this alternate embodiment, the coupler or rail-engagement mechanism on the sealing member of the laryngeal airway device includes a pair of opposing brackets 80 on the distal portion of the sealing member, near the edges 23, between the lateral flanges 24 and the distal end 22. Each bracket includes a first wall portion 81 that rises from the anterior support surface 21 near an edge 23 of the support member 16, and a medially-extending portion 83 that is oriented toward the medially-extending portion of the opposing bracket. FIG. 19B is a rear perspective view of the laryngeal airway device coupled to the introducer 11. FIG. 19C shows a front cross-sectional view of the introducer 11 with the distal portion of the laryngeal airway device 10 coupled to it; this view is along line C—C of FIG. 19B. In this embodiment, the introducer 11 is identical in most respects with the embodiment of the introducer illustrated in FIGS. 4–6, 7 and 9. The exception is in the structure of the track in the embodiment illustrated in FIG. 19B. The track of the introducer 11 in FIG. 19B includes two opposing slide rails that are formed by upwardly extending wall portions 47, which transition to outwardly-extending sections 85. The outwardly-extending sections 85 of the track engage the medially-extending portions 83 of the opposing brackets 80, permitting the laryngeal airway device to engage and slidably move along the track from the proximal to the distal end of the introducer 11. At the distal end of the introducer, the widths of the outwardly-extending portions 85 reduce medially until only the upward extensions 47 remain, thereby permitting the laryngeal airway device to disengage from the introducer 11.

Many variations of the coupler/track combination are possible. Not all are included in the embodiments that have been illustrated and described. Possible alternate embodiments could include a track with a single rail on the posterior side of the introducer and a coupler on the sealing member that is adapted to engage it.

The coupling and tracking features of this invention may also be applied to laryngeal blade technology that is known in the art, by applying a track to a blade. In this regard, FIGS. 20A–20D show a laryngoscope 80 having a handle 82 and a curved blade 84 with a fiberoptic channel 85 disposed thereon. The handle 82 may be conventionally detachably joined to the blade 84 by a mechanism including elements 86a and 86b. The blade 84 preferably has the shape of a capital "J" in a side elevation. The blade 84 includes an anterior surface 88 and a posterior side 89. A track 96 is formed on the posterior side 89. The track 96 is constructed in the same manner as the track 46 on the introducer 11. So modified, the blade 84 will have the form and function of the introducer that are necessary for guiding or tracking. Therefore, a laryngeal airway device 10 with a coupler 25 may be slidably coupled to the track 96 and guided thereby in the manner and for the purpose discussed above. The track 96 is shown in cross-section in FIG. 20D with the tab 26 of the flange 25 coupled thereto. Manifestly, the invention therefore may be practiced using as an introducer a blade device having a track formed thereon. It should be evident that the track on the laryngeal blade device may have either embodiment discussed above, and any equivalent thereof. Further, the distal end of the blade 84 may be modified to accommodate the vallecular engagement features discussed above.

Clearly, many other embodiments and modifications of this invention will occur readily to those of ordinary skill in the art in view of these teachings. Therefore, this invention is to be limited only by following claims, which include all such embodiments and modifications when viewed in conjunction with the above specification and accompanying drawings.

We claim:

1. A laryngeal airway device, comprising:
   an air tube with two ends;
   a sealing member mounted to the air tube, near an end of the air tube, including:
   a compressible pad;
   a support member adjacent to the pad;
   and, a flexible flange on the support member for coupling the device to an introducer.

2. The device of claim 1, wherein the flexible flange is moveable from a first position relative to said support member to a second position relative to said support member.

3. The device of claim 2, wherein the flexible flange includes a pedestal connected to a tab, at least a portion of the pedestal being narrower than the tab.

* * * * *